US012479803B2

(12) United States Patent
Chakrabarti et al.

(10) Patent No.: US 12,479,803 B2
(45) Date of Patent: Nov. 25, 2025

(54) ANTIMALARIAL COMPOUNDS

(71) Applicant: UNIVERSITY OF CENTRAL FLORIDA RESEARCH FOUNDATION, INC., Orlando, FL (US)

(72) Inventors: Debopam Chakrabarti, Orlando, FL (US); Yu Yuan, Orlando, FL (US); Guang Huang, Orlando, FL (US); Claribel Murillo Solano, Orlando, FL (US)

(73) Assignee: UNIVERSITY OF CENTRAL FLORIDA RESEARCH FOUNDATION, INC., Orlando, FL (US)

( * ) Notice: Subject to any disclaimer, the term of this patent is extended or adjusted under 35 U.S.C. 154(b) by 1028 days.

(21) Appl. No.: 17/601,151

(22) PCT Filed: Apr. 3, 2020

(86) PCT No.: PCT/US2020/026576

§ 371 (c)(1),
(2) Date: Oct. 4, 2021

(87) PCT Pub. No.: WO2020/206252

PCT Pub. Date: Oct. 8, 2020

(65) Prior Publication Data

US 2022/0204452 A1 Jun. 30, 2022

Related U.S. Application Data

(60) Provisional application No. 62/828,765, filed on Apr. 3, 2019.

(51) Int. Cl.

| | |
|---|---|
| ***C07D 215/46*** | (2006.01) |
| ***A61P 33/06*** | (2006.01) |
| ***C07D 401/04*** | (2006.01) |
| ***C07D 401/06*** | (2006.01) |
| ***C07D 405/06*** | (2006.01) |
| ***C07D 409/06*** | (2006.01) |
| ***C07D 417/06*** | (2006.01) |

(52) U.S. Cl.

CPC ............ *C07D 215/46* (2013.01); *A61P 33/06* (2018.01); *C07D 401/04* (2013.01); *C07D 401/06* (2013.01); *C07D 405/06* (2013.01); *C07D 409/06* (2013.01); *C07D 417/06* (2013.01)

(58) Field of Classification Search

CPC .. C07D 215/46; C07D 401/04; C07D 401/06; C07D 405/06; C07D 409/06; C07D 417/06; A61P 33/06

See application file for complete search history.

(56) References Cited

U.S. PATENT DOCUMENTS 9,249,103 B2 * 2/2016 Riscoe .................. A61K 31/47

FOREIGN PATENT DOCUMENTS

| | | | |
|---|---|---|---|
| CN | 103172577 A | * | 6/2013 |
| WO | 202020622 A1 | | 10/2020 |

OTHER PUBLICATIONS

Purser et al., Chem. Soc. Rev., 2008,37,320-330 (Year: 2008).*
Berge et al., Journal of Pharmaceutical Sciences, 1977,66, 1-19 (Year: 1977).*
Foley et al., Pharmacol. Ther., 1998, 79, 55-87 (Year: 1998).*
Han et al., AAPS Pharmsci., 2000, 2, 1-11 (Year: 2000).*
Testa, Biochem. Pharm., 2004, 68, 2097-2106 (Year: 2004).*
Han, H., AAPS Pharmsci., 2000, 2, 1-11 (Year: 2000).*
PCT Search Report & Written Opinion, PCT/US2020/026576, dated Jul. 21, 2020, 6 pages.
Roberts, Bracken F. et al., "4-Nitro styrylquinoline is an antimalarial inhibiting multiple stages of Plasmodium flaciparum asexual life cycle", International Journal for Parasitology: Drugs and Drugs Resistance vol. 7, 2017, pp. 120-129.

* cited by examiner

*Primary Examiner* — John S Kenyon
*Assistant Examiner* — Sara Elizabeth Bell
(74) *Attorney, Agent, or Firm* — Timothy H. Van Dyke; Wolter Van Dyke; Davis, Pllc

(57) ABSTRACT

Antimalarial compounds of the formula: in which n is 1 or 2; X is C or N; $R_1$ is a moiety comprising a secondary amine and a tertiary amine joined by a $C_2$ to $C_4$ alkyl chain; and $R_2$ is $CF_3$, F, or H, or an analog, combination, derivative, prodrug, stereoisomer, or pharmaceutically acceptable salt thereof. Pharmaceutical compounds including the antimalarial compounds. Methods of treating or preventing malaria comprising administering an effective amount of the antimalarial compounds.

(I)

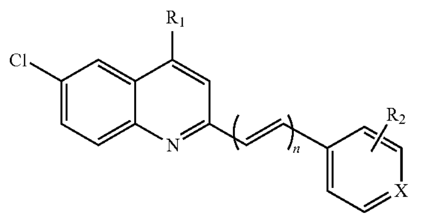

12 Claims, 9 Drawing Sheets

FIG. 3A: 6 hours exposure
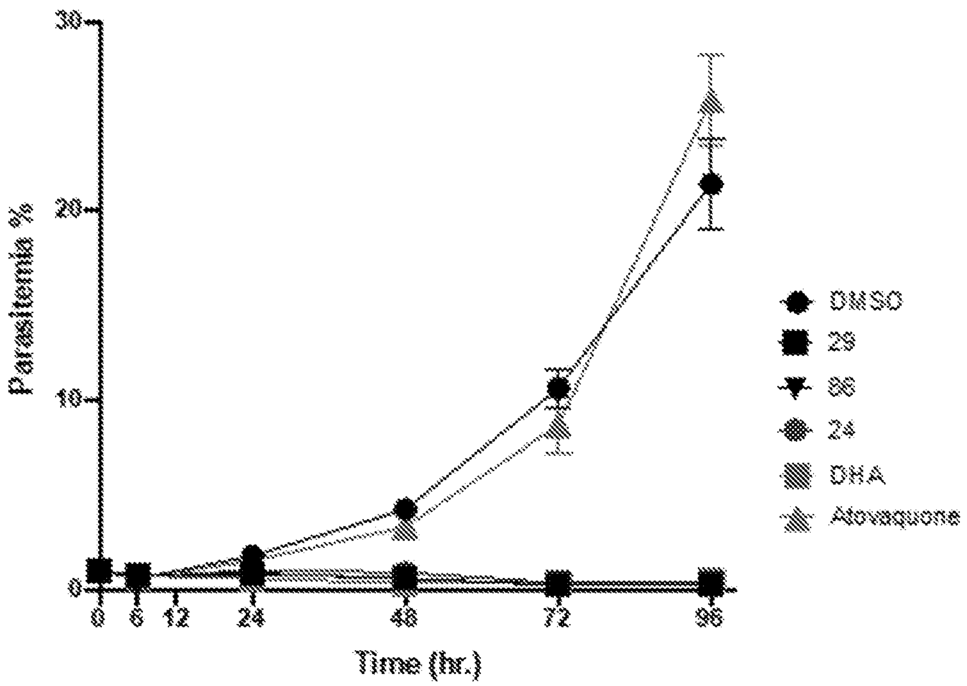
FIG. 3B: 12 hours exposure
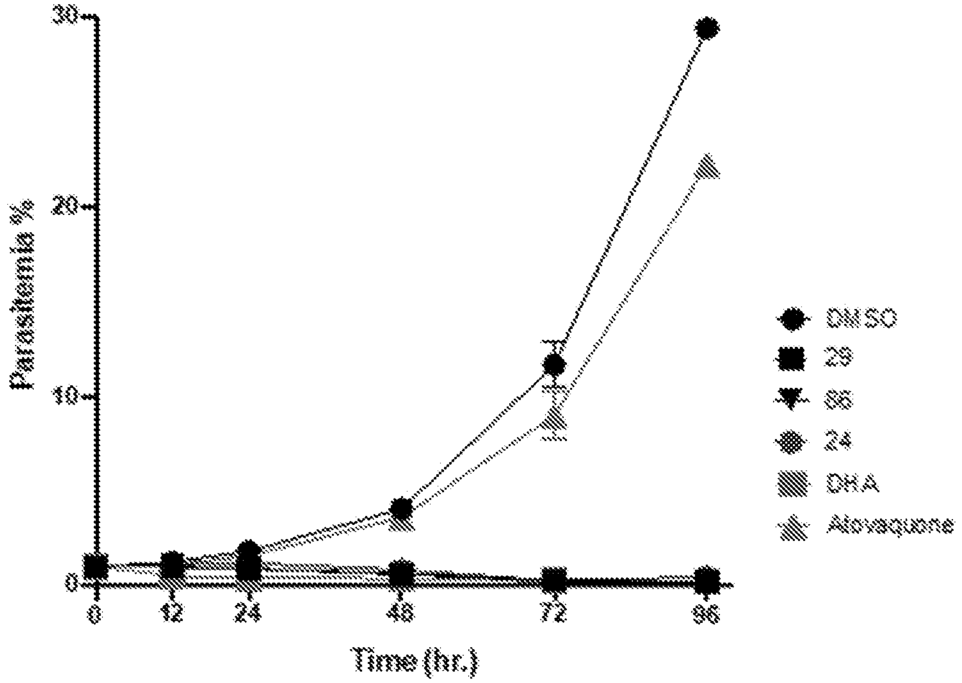

FIG. 3C: 24 hours exposure
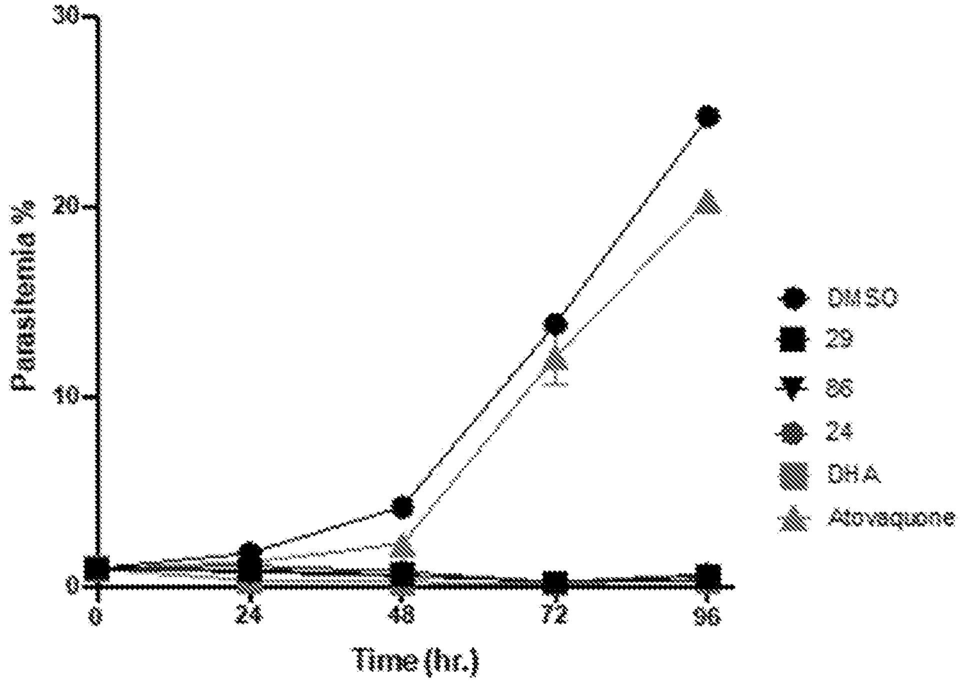
FIG. 3D: 48 hours exposure
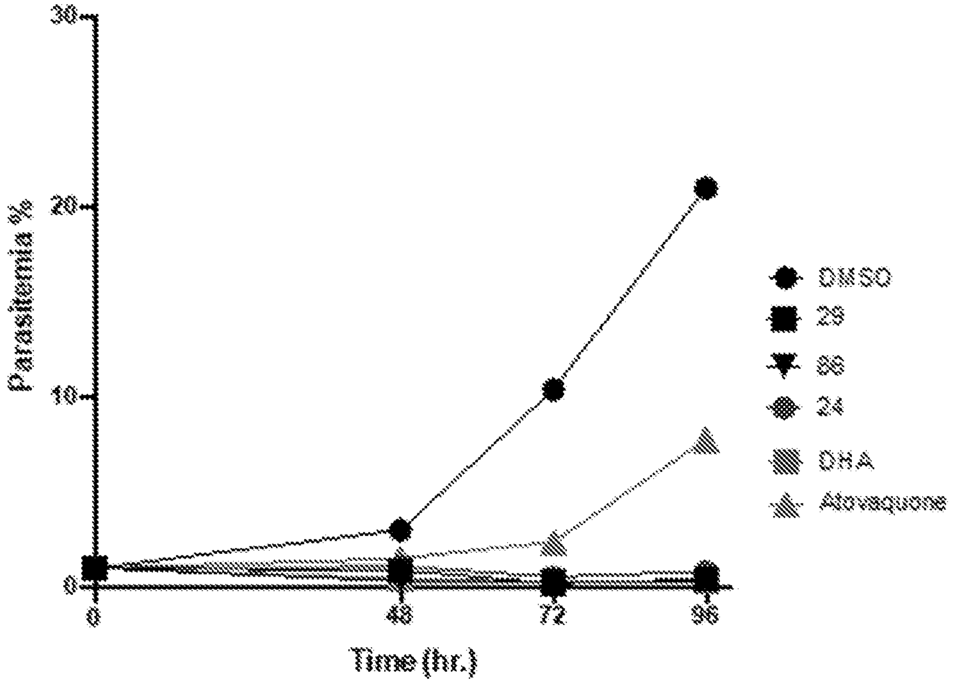

ANTIMALARIAL COMPOUNDS

CROSS-REFERENCE TO RELATED APPLICATION

This application claims the benefit of U.S. Provisional Patent Application No. 62/828,765, filed Apr. 3, 2019, titled ANTIMALARIAL COMPOUNDS, which is incorporated by reference herein in its entirety.

STATEMENT REGARDING FEDERALLY SPONSORED RESEARCH OR DEVELOPMENT

This invention was made with government support under NIH/NIAID AI117298 awarded by the National Institute of Allergy and Infectious Diseases. The government has certain rights in this invention.

FIELD OF THE INVENTION

The present invention relates to the field of infectious diseases and, more particularly, to malaria and to antimalarial compounds.

BACKGROUND

Malaria is a vector-borne protozoan disease. Malaria is one of the most prevalent parasitic infections for mankind, with over 40% of the world's population at risk for malaria. The parasite is transmitted by mosquitoes in many tropical and subtropical regions. Human malaria, a tropical infectious disease, is mainly caused by five species of protozoan parasites of the genus *Plasmodium*, with *P. falciparum* being the most virulent and fatal species. Malaria is initiated when *Plasmodium* sporozoites are transmitted to the human host during the blood feeding of infected female *Anopheles* mosquitos. Upon transmission, sporozoites invade hepatocytes, develop into merozoites, and eventually release into the bloodstream. Then the released merozoites replicate in the erythrocytes, causing malaria-associated clinical manifestations. Some merozoites differentiate into gametocytes. Transmission of the parasites to the vectors occurs when *Anopheles* mosquitos ingest the gametocytes during a blood meal, instigating the sexual sporogonic cycle.

The most common symptoms of malaria include a flu-like illness with fever, shivering, vomiting, nausea, joint pain, muscle aches, and headaches. The classical symptom of malaria is the cycle of sudden chill with shivering followed by fever and then sweating persisting for six to ten hours. Other symptoms experienced by malaria patients include dizziness, malaise, myalgia, abdominal pain, mild diarrhea, and dry cough. The causative organism of severe malaria is, typically, *P. falciparum* and consequences include coma and death if untreated. Other complications of severe malaria may occur and include splenomegaly, cerebral ischemia, hepatomegaly, hypoglycemia, hemoglobinuria, renal failure, pulmonary edema, and acidosis.

The World Health Organization estimates that there were 219 million clinical episodes and 435,000 deaths from malaria in 2018, predominantly among children below age of five years and pregnant women in Africa. Significant progress has been made in the reduction of the global malaria burden over the last decade owing to the use of artemisinin-based combination therapy (ACT) and long-lasting insecticide treated nets as well as indoor residual spraying for vector control. However, the cost prohibitive restriction of ACTs' broad use in low-income malaria-endemic countries and more disturbingly, the loss of efficacy of frontline ACTs to the resistant malaria strains underscore the fragility of gains in the global malaria eradication efforts. To address the detrimental situation and achieve the eventual elimination of malaria, it is important for pharmaceutical industry and academic labs to develop inexpensive chemical scaffolds against drug-resistant malaria strains with new mechanisms of action, ideally possessing transmission-blocking properties.

An important strategy to develop new antimalarial compounds involves structural re-engineering of exiting drugs like Chloroquine (CQ), a landmark compound due to its efficacy against all types of human malaria parasites, long half-life, low cost and safety profiles. Mutations in the gene encoding the digestive vacuole (DV) membrane protein PfCRT is responsible for CQ resistance, which cause reduced drug accumulation in its site of action. Based on this premise, numerous of CQ analogs with the conformational rigidity of nitrogen-containing side chain and CQ hybrids (CQ-resistance reverse agents, CQ-artemisinin, CQ-synthetic peroxide, CQ-ferrocene, CQ-chalcone, CQ-N-contained heterocyclic compound, etc.) have been developed to overcome the resistance and improve the antiplasmodial activity. Piperaquine and Ferroquine are examples of re-engineered CQ analogues. The former containing two 7-chloro-aminoquinoline moieties is extensively used in east Asia as prophylaxis and treatment. The latter, a 7-chloro-aminoquinoline covalently linked to an aminoferrocene group, is currently in phase II pilot clinical trials. Thus, quinoline scaffold is a privileged structure that holds the potential to new antimalarial candidates.

Often a combination of drugs is preferred because different modes of action are combined to aid in inhibiting the emergence of drug resistant parasites. Therefore, ongoing development of compounds that may be used alone or in combination with other compounds is essential. A 4-nitrostyrylquinoline analogue (Formula 1) has recently exhibited promising antimalaria activity and excellent selectivity.

Formula 1

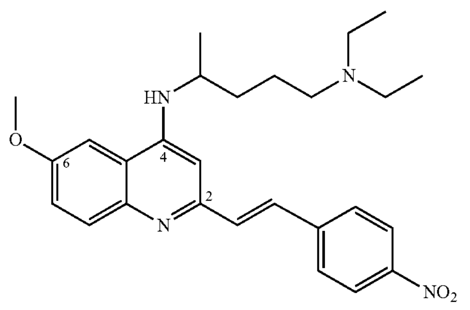

In addition to the need for new compounds to facilitate the combination of drugs with different modes of action, a need also exists for continued development of new antimalarial compounds because the effectiveness of current antimalarial therapies is under threat by the spread of drug-resistant parasites. Even the effectiveness of gold-standard antimalarial drugs (artemisinin-based combination treatments, ACTs) is threatened by continued emergence and spread of drug-resistant parasites. The development of such resistance poses one of the greatest threats to malaria control and results in increased malaria morbidity and mortality. Despite intensive research extending back to the 1930s, when the first synthetic antimalarial drugs made their appearance, the repertoire of clinically licensed formulations remains very limited. Moreover, widespread and increasing resistance to these drugs contributes enormously to the difficulties in controlling malaria, posing considerable intellectual, technical and humanitarian challenges. For at least these reasons, a pressing need exists for new antimalarial compounds.

BRIEF SUMMARY

Detailed structure-activity relationship studies of 2-arylvinylquinolines were conducted leading to the discovery of potent, low nanomolar antimalarial compounds against chloroquine-resistant Dd2 strain, with excellent selectivity profiles (RI<1 and SI>200). Several metabolically stable 2-arylvinylquinolines are identified as fast-acting antimalarial agents that kill asexual blood stage parasites at the trophozoite phase, and the most promising compound 24 also demonstrates good transmission blocking potential. Additionally, the phosphate salt of 24 exhibits exceptional in vivo antimalarial efficacy in the murine model without noticeable toxicity. Thus, the 2-arylvinylquinolines, according to various embodiments, represent a promising class of compounds for the development of new antimalarial treatments.

Various embodiments relate to compounds according to Formula 2.

Formula 2

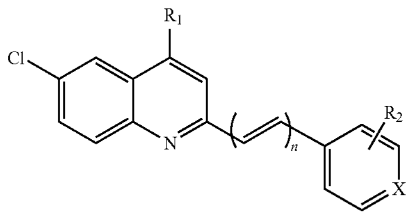

in which, n may be 1 or 2; X may be C or N; $R_1$ may be a moiety comprising a secondary amine and a tertiary amine joined by a $C_2$ to $C_4$ alkyl chain; and $R_2$ may be $CF_3$, F, or H. Multiple $R_2$ groups may be present. According to various embodiments, $R_1$ may be

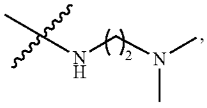

,

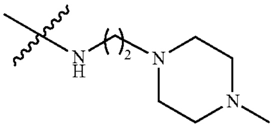

, or

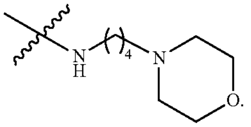

Analogs, derivatives, prodrugs, stereoisomers, or pharmaceutically acceptable salts of the compounds according to Formula 2 are also within the scope of the present invention.

The compounds according to various embodiments may exhibit antiplasmodium potency against chloroquine-resistant (Dd2) strains of *P. falciparum*. For example, the compounds may exhibit an $IC_{50}$ against chloroquine-resistant (Dd2) strains of *P. falciparum* of less than or equal to 15 nM.

Various embodiments relate to pharmaceutical compositions comprising an effective amount of one or more of the compounds according to various embodiments or analogs, combinations, derivatives, prodrugs, stereoisomers, or pharmaceutically acceptable salts thereof. The pharmaceutical compositions may exhibit antiplasmodium potency against chloroquine-resistant (Dd2) strains of *P. falciparum*. For example, the pharmaceutical compositions may exhibit an $IC_{50}$ against chloroquine-resistant (Dd2) strains of *P. falciparum* of less than or equal to 15 nM. According to various embodiments, the pharmaceutical compositions may further comprise a pharmaceutically acceptable carrier and/or a conjunctive anti-malarial agent.

Various embodiments relate to methods of treating malaria, comprising administering to a subject an effective amount of a compound according to any of the various embodiments and/or a pharmaceutical composition comprising a compound according to any of the various embodiments.

These and other features, aspects, and advantages of various embodiments will become better understood with reference to the following description, figures, and claims.

BRIEF DESCRIPTION OF THE FIGURES

Many aspects of this disclosure can be better understood with reference to the following figures, in which:

FIG. 3A: is an example according to various embodiments illustrating rate of killing and parasitocidal/parasitostatic activity determination of arylvinylquinolines. The killing rate was evaluated in asynchronous Dd2 parasite cultures exposed to $5\times EC_{50}$ concentration for 6 h;

FIG. 3B: is an example according to various embodiments illustrating rate of killing and parasitocidal/parasitostatic activity determination of arylvinylquinolines. The killing rate was evaluated in asynchronous Dd2 parasite cultures exposed to $5\times EC_{50}$ concentration for 12 h;

FIG. 3C: is an example according to various embodiments illustrating rate of killing and parasitocidal/parasitostatic activity determination of arylvinylquinolines. The killing rate was evaluated in asynchronous Dd2 parasite cultures exposed to $5\times EC_{50}$ concentration for 24 h;

FIG. 3D: is an example according to various embodiments illustrating rate of killing and parasitocidal/parasitostatic activity determination of arylvinylquinolines. The killing rate was evaluated in asynchronous Dd2 parasite cultures exposed to $5\times EC_{50}$ concentration for 48 h;

Figure 1:
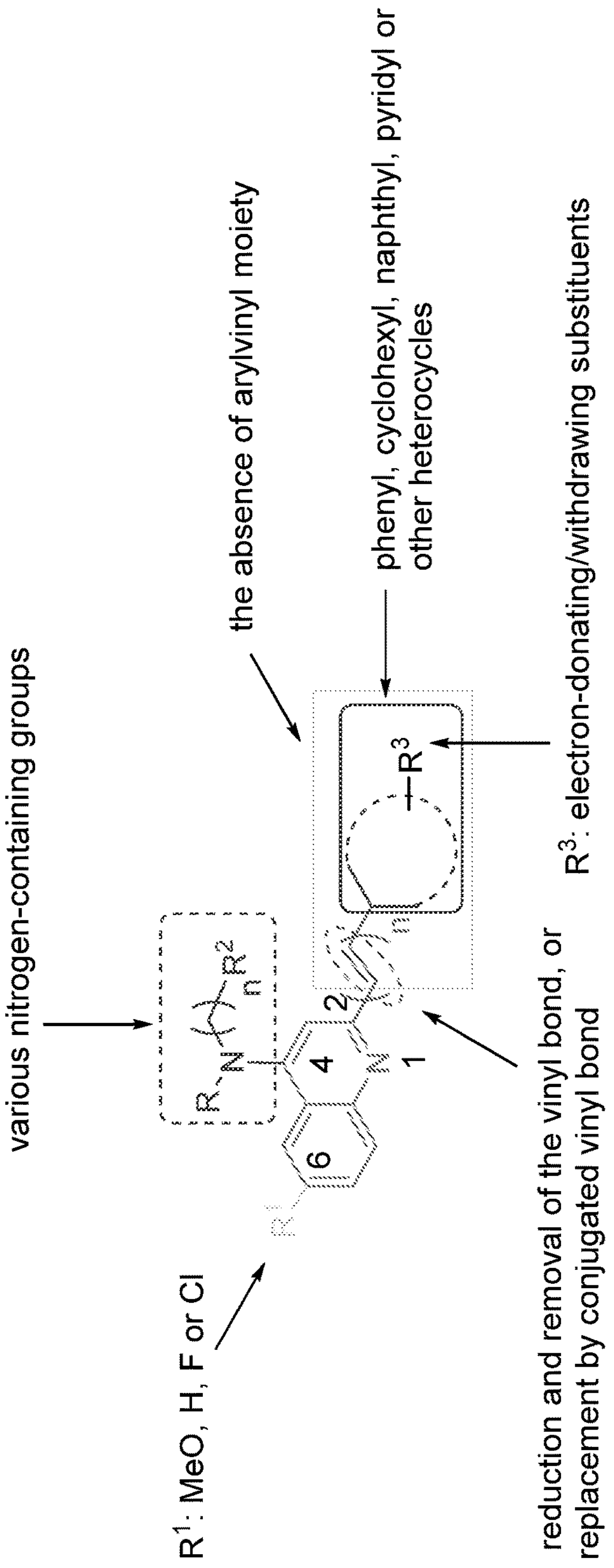
FIG. 1: is an example according to various embodiments, illustrating a schematic representation of Structure-Activity Relationship (SAR) strategy explored around the quinoline scaffold.

It should be understood that the various embodiments are not limited to the examples illustrated in the figures.

DETAILED DESCRIPTION

Introduction and Definitions

Various embodiments may be understood more readily by reference to the following detailed description. Unless defined otherwise, all technical and scientific terms used herein have the same meaning as commonly understood by one of ordinary skill in the art to which this disclosure belongs.

As used herein, the term "standard temperature and pressure" generally refers to 25° C. and 1 atmosphere. Standard temperature and pressure may also be referred to as "ambient conditions." Unless indicated otherwise, parts are by weight, temperature is in ° C., and pressure is at or near atmospheric. The terms "elevated temperatures" or "high-temperatures" generally refer to temperatures of at least 100° C.

The term "mol percent" or "mole percent" generally refers to the percentage that the moles of a particular component are of the total moles that are in a mixture. The sum of the mole fractions for each component in a solution is equal to 1.

It is to be understood that this disclosure is not limited to particular embodiments described, as such may, of course, vary. It is also to be understood that the terminology used herein is for the purpose of describing particular embodiments only, and is not intended to be limiting, since the scope of the present disclosure will be limited only by the appended claims.

All numeric values are herein assumed to be modified by the term "about," whether or not explicitly indicated. The term "about" generally refers to a range of numbers that one of skill in the art would consider equivalent to the recited value (i.e., having the same function or result). In many instances, the term "about" may include numbers that are rounded to the nearest significant figure.

Where a range of values is provided, it is understood that each intervening value, to the tenth of the unit of the lower limit (unless the context clearly dictates otherwise), between the upper and lower limit of that range, and any other stated or intervening value in that stated range, is encompassed within the disclosure. The upper and lower limits of these smaller ranges may independently be included in the smaller ranges and are also encompassed within the disclosure, subject to any specifically excluded limit in the stated range. Where the stated range includes one or both of the limits, ranges excluding either or both of those included limits are also included in the disclosure.

All publications and patents cited in this specification are herein incorporated by reference as if each individual publication or patent were specifically and individually indicated to be incorporated by reference and are incorporated herein by reference to disclose and describe the methods and/or materials in connection with which the publications are cited. The citation of any publication is for its disclosure prior to the filing date and should not be construed as an admission that the present disclosure is not entitled to antedate such publication by prior disclosure. Further, the dates of publication provided could be different from the actual publication dates that may need to be independently confirmed.

Unless otherwise indicated, the present disclosure is not limited to particular materials, reagents, reaction materials, manufacturing processes, or the like, as such can vary. It is also to be understood that the terminology used herein is for purposes of describing particular embodiments only and is not intended to be limiting. It is also possible in the present disclosure that steps can be executed in different sequence where this is logically possible.

It must be noted that, as used in the specification and the appended claims, the singular forms "a," "an," and "the" include plural referents unless the context clearly dictates otherwise. Thus, for example, reference to "a support" includes a plurality of supports. In this specification and in the claims that follow, reference will be made to a number of terms that shall be defined to have the following meanings unless a contrary intention is apparent.

All the features disclosed in this specification (including any accompanying claims, abstract, and drawings) may be replaced by alternative features serving the same, equivalent or similar purpose, unless expressly stated otherwise. Thus, unless expressly stated otherwise, each feature disclosed is one example only of a generic series of equivalent or similar features.

The examples and embodiments described herein are for illustrative purposes only and that various modifications or changes in light thereof will be suggested to persons skilled in the art and are to be included within the spirit and purview of this application. Many variations and modifications may be made to the above-described embodiment(s) of the disclosure without departing substantially from the spirit and principles of the disclosure. All such modifications and variations are intended to be included herein within the scope of this disclosure.

Various embodiments are described by reference to chemical structures. In the chemical structures various chemical moieties are represented by R-groups. Some R-groups are described by reference to another chemical structure. A wavy bond line in a structure representing an R-group indicates the point at which the R-group is attached to or bonded to the main structure. In some chemical structures various cyclic moieties are represented by lettered rings. The lettered ring may represent a variety of cyclic structures. Some cyclic structures are described by reference to another chemical structure. A wavy bond line in a structure representing a cyclic structure indicates a bond that is shared with the main structure, or the point at which the cyclic structure is fused to the main structure to form a polycyclic structure. Various subscripts are also used. Each R-group has a numeric subscript which distinguishes it from other R-groups. R-groups and lettered rings may also include a lowercase alphabetical subscript, indicating that different embodiments, may have differing numbers of that moiety. If a lowercase alphabetical subscript may be 0, it means that, in some embodiments, the moiety may not be present. A dashed line in a cyclic structure indicates that in various embodiments one or more double-bounds may be present. When a compound may include more than one instance of a moiety, for example a moiety represented by an R-group, and that moiety is described as being "independently selected" from a list of options, each instance may be selected from the complete list without respect to any prior selections from the list; in other words, the instances may be the same or different and the same list item may be selected for multiple instances. Some R-group substitutions indicate a range, such as $C_1$-$C_6$ alkyl. Such a range indicates that the R-group may be a $C_1$ alkyl, a $C_2$ alkyl, a $C_3$ alkyl, a $C_4$ alkyl, a $C_5$ alkyl, or a $C_6$ alkyl. In other words, all such ranges are intended to include an explicit reference to each member within the range.

As used herein, the term "secondary amine" refers to an amino group in which a nitrogen atom is directly bonded to two carbons of any hybridization, with the proviso that these carbons may not be carbonyl group carbons. Structure A provides an illustration:

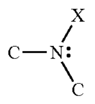

(A)

Referring to Structure A, X may be any atom but carbon and is usually hydrogen. C may be any carbon group except carbonyl. A carbonyl group refers to a functional group composed of a carbon atom double-bonded to an oxygen atom As used herein, the term "tertiary amine" refers to an amino group in which the nitrogen atom is directly bonded to three carbons of any hybridization, with the proviso that these carbons may not be carbonyl group carbons. Structure B provides an illustration:

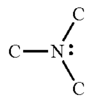

(B)

Referring to Structure B, C may be any carbon group except carbonyl.

As used herein, "alkyl" refers to an unbranched or branched hydrocarbon chain. An alkyl group may be unsubstituted or substituted with one or more heteroatoms.

As used herein, "aryl" refers to aromatic monocyclic or multicyclic groups containing from 6 to 19 carbon atoms. Aryl groups include but are not limited to groups such as unsubstituted or substituted fluorenyl, unsubstituted or substituted phenyl, and unsubstituted or substituted naphthyl.

As used herein, "heteroaryl" refers to a monocyclic or multicyclic aromatic ring system, in certain embodiments, of about 5 to about 15 members where one or more, in one embodiment 1 to 3, of the atoms in the ring system is a heteroatom, that is, an element other than carbon, including but not limited to, nitrogen, oxygen or sulfur. The heteroaryl group may be optionally fused to a benzene ring. Heteroaryl groups include, but are not limited to, furyl, imidazolyl, pyrimidinyl, tetrazolyl, thienyl, pyridyl, pyrrolyl, thiazolyl, isothiazolyl, oxazolyl, isoxazolyl, triazolyl, quinolinyl or isoquinolinyl.

As used herein, solvent refers to any liquid that completely or partially dissolves a solid, liquid, or gaseous solute, resulting in a solution such as but not limited to hexane, benzene, toluene, diethyl ether, chloroform, ethyl acetate, dichloromethane, carbon tetrachloride, 1,4-dioxane, tetrahydrofuran, glyme, diglyme, acetone, acetonitrile, dimethylformamide, dimethyl sulfoxide, dimethylacetamide, or N-methyl-2-pyrrolidone.

It is to be understood that reactants, compounds, solvents, acids, bases, catalysts, agents, reactive groups, or the like may be added individually, simultaneously, separately, and in any order. Furthermore, it is to be understood that reactants, compounds, acids, bases, catalysts, agents, reactive groups, or the like may be pre-dissolved in solution and added as a solution (including, but not limited to, aqueous solutions). In addition, it is to be understood that reactants, compounds, solvents, acids, bases, catalysts, agents, reactive groups, or the like may be in any molar ratio.

It is to be understood that reactants, compounds, solvents, acids, bases, catalysts, agents, reactive groups, or the like may be formed in situ.

As used herein, the term "malaria" refers to an infectious disease spread by mosquitoes and caused by parasites of the genus *Plasmodium.*

As used herein, the term "parasite" refers to microorganisms that generally exploit the resources of its host body. Parasites may show a high degree of specialization and reproduce faster than their host. Parasites may also kill or reduce the biological mechanisms of the hosts.

As used herein, the terms "administering" or "administration" of a composition or a compound or an agent as described herein to a subject includes any route of introducing or delivering to a subject a compound to perform its intended function. The administering or administration can be carried out by any suitable route, including orally, intranasally, parenterally (intravenously, intramuscularly, intraperitoneally, or subcutaneously), rectally, or topically. Administering or administration includes self-administration and the administration by another.

As used herein, the terms "treating" or "treatment" or "alleviation" refers to both therapeutic treatment and prophylactic or preventative measures, wherein the objective is to prevent or slow down (lessen) the targeted pathologic condition or disorder.

As used herein, the term "preventing" means causing the clinical symptoms of the disease state not to worsen or develop, e.g., inhibiting the onset of disease, in a subject that may be exposed to or predisposed to the disease state, but does not yet experience or display symptoms of the full disease state, e.g., malaria.

According to certain embodiments, provided are methods of preventing or treating malaria in a subject or preventing or treating a subject exhibiting a symptom of malaria by administering effective amounts of one or more compounds described herein. Malaria typically produces a string of recurrent attacks, or paroxysms, each of which has three stages—chills, followed by fever, and then sweating. Along with chills, the person is likely to have headache, malaise, fatigue, muscular pains, occasional nausea, vomiting, and diarrhea. Within an hour or two, the body temperature rises, and the skin feels hot and dry. Then, as the body temperature falls, a drenching sweat begins. The person, feeling tired and weak, is likely to fall asleep. A subject exhibiting one, two or more of the foregoing symptoms is considered a subject in need.

As used herein, "anti-malarial" or "anti-malarial activity" includes any activity that decreases the infectivity, the reproduction, or inhibits the progress of the lifecycle of a malaria parasite. "Anti-malarial activity" includes inhibition of the growth of malaria infection by all of the means of observed with current anti-malarial drugs.

As used herein, the term "anti-malarial agent" refers to any compound according to the various embodiments, compounds referred to in the Tables below, and any combinations, prodrugs, pharmaceutically acceptable salts, analogs, and derivatives thereof.

The compositions and methods described herein may be useful for the treatment and/or prevention of malaria. The determination of a therapeutically effective dose is well within the capability of those skilled in the art. A therapeutically effective dose refers to that amount of active ingredient which causes reduction or elimination of malaria in a subject.

As used herein, by the term "effective amount," "amount effective," "therapeutically effective amount," or the like, it is meant an amount effective at dosages and for periods of time necessary to achieve the desired result.

For any compound, the therapeutically effective dose can be estimated initially either in cell culture assays or in animal models, usually mice, rabbits, dogs, or pigs. The animal model also can be used to determine the appropriate concentration range and route of administration. Such information can then be used to determine useful doses and routes for administration in humans.

Therapeutic efficacy and toxicity, e.g., $ED_{50}$ (the dose therapeutically effective in 50% of the population) and $LD_{50}$ (the dose lethal to 50% of the population), can be determined by standard pharmaceutical procedures in cell cultures or experimental animals. The dose ratio of toxic to therapeutic effects is the therapeutic index, and it can be expressed as the ratio, $LD_{50}/ED_{50}$.

The half maximal inhibitory concentration ($IC_{50}$) is a measure of the potency of a substance in inhibiting a specific biological or biochemical function. $IC_{50}$ is a quantitative measure that indicates how much of a particular inhibitory substance is needed to inhibit, in vitro, a given biological process or biological component by 50%.

Pharmaceutical compositions which exhibit large therapeutic indices are preferred. The data obtained from cell culture assays and animal studies may be used in formulating a range of dosage for human use. The dosage contained in such compositions is preferably within a range of circulating concentrations that include the $ED_{50}$ with little or no toxicity. The dosage varies within this range depending upon the dosage form employed, sensitivity of the patient, and the route of administration. The toxicity of the present compounds of this invention can be further modulated by terminal N-alkylation. For example, polyamine compounds containing N-methyl groups are most stable to amine oxidases and are less toxic (see Designing the Polyamine Pharmacophore: Influence of N-substituents on the transport behavior of polyamine conjugates, Kaur, N.; Delcros, J-G.; Archer, J.; Weagraff, N. Z.; Martin, B.; Phanstiel IV, O. *J. Med. Chem.* 2008, 51, 2551-2560.). These insights can be applied to the other compounds described herein. For example, tertiary amine systems should be stable to amine oxidases. In addition, methyl esters are less toxic than the free carboxylic acid form of the novel compositions (described herein in vitro) and provide an approach for lowered toxicity and pro-drug designs reliant upon hydrolysis or esterase activity in vivo to liberate the active carboxylic acid form.

The exact dosage will be determined by the practitioner, in light of factors related to the subject that requires treatment. Dosage and administration are adjusted to provide sufficient levels of the active ingredient or to maintain the desired effect. Factors which can be taken into account include the severity of the disease state, general health of the subject, age, weight, and gender of the subject, diet, time and frequency of container and labeled for treatment of an indicated condition. Such labeling would include amount, frequency, and method of administration.

Normal dosage amounts can vary from 0.1 to 100,000 micrograms, up to a total dose of about 1 g, depending upon the route of administration and duration of therapy. Guidance as to particular dosages and methods of delivery is provided in the literature and generally available to practitioners in the art. Those skilled in the art will employ different formulations for nucleotides than for proteins or their inhibitors.

As used herein, the term "subject" refers to any animal (e.g., a mammal), including, but not limited to, humans, which may be the recipient of a particular treatment. The term is intended to include living organisms susceptible to conditions or diseases caused or contributed to by unrestrained cell proliferation and/or differentiation where control of polyamine transport is required. Examples of subjects include, but are not limited to, humans, dogs, cats, horses, cows, goats, sheep, and mice. As used herein, the terms "treating" or "treatment" refer to both therapeutic treatment and prophylactic or preventative measures, wherein the object is to prevent or slow down (lessen) the targeted pathologic condition or disorder.

The compositions described herein may comprise an antimalarial compound as described herein. In one embodiment, there are provided pharmaceutical compositions comprising a compound according the various embodiments, or combinations, analogs, derivatives, prodrugs, stereoisomers, or pharmaceutically acceptable salts thereof, which can be administered to a patient to achieve a therapeutic effect. In a particular embodiment, the pharmaceutical compound comprises a compound according to any of the various embodiments, or an analog, a derivative, a prodrug, a stereoisomer, or a pharmaceutically acceptable salt thereof. The compositions may be administered alone or in combination with at least one other agent, such as a stabilizing compound, which can be administered in any sterile, biocompatible pharmaceutical carrier, including, but not limited to, saline, buffered saline, dextrose, and water. The compositions can be administered to a patient alone, or in combination with other agents, drugs, and/or hormones.

As used herein, the terms "composition" or "pharmaceutical composition" comprises one or more of the compounds described herein as active ingredient(s), or a pharmaceutically acceptable salt(s) thereof, and may also contain a pharmaceutically acceptable carrier and optionally other therapeutic ingredients. The compositions include compositions suitable for oral, rectal, ophthalmic, pulmonary, nasal, dermal, topical, parenteral (including subcutaneous, intramuscular and intravenous) or inhalation administration. The most suitable route in any particular case will depend on the nature and severity of the conditions being treated and the nature of the active ingredient(s). The compositions may be presented in unit dosage form and prepared by any of the methods well-known in the art of pharmacy. Dosage regimes may be adjusted for the purpose to improving the therapeutic response. For example, several divided dosages may be administered daily or the dose may be proportionally reduced over time. A person skilled in the art normally may determine the effective dosage amount and the appropriate regime.

As used herein, the term "analog" refers to a compound having a structure similar to that of another compound but differing from the other compound with respect to a certain component or substituent. The compound may differ in one or more atoms, functional groups, or substructures, which may be replaced with other atoms, groups, or substructures. In one aspect, such structures possess at least the same or a similar therapeutic efficacy.

As used herein, "derivative" refers to a compound derived or obtained from another and containing essential elements of the parent compound. In one aspect, such a derivative possesses at least the same or similar therapeutic efficacy as the parent compound.

As used herein, the term "pharmaceutically acceptable salt" is intended to include nontoxic base addition salts. Suitable salts include those derived from organic and inorganic acids such as, without limitation, hydrochloric acid, hydrobromic acid, phosphoric acid, sulfuric acid, methanesulfonic acid, acetic acid, tartaric acid, lactic acid, sulfinic acid, citric acid, maleic acid, fumaric acid, sorbic acid, aconitic acid, salicylic acid, phthalic acid, and the like. The term "pharmaceutically acceptable salt" as used herein is also intended to include salts of acidic groups, such as a carboxylate, with such counterions as ammonium, alkali metal salts, particularly sodium or potassium, alkaline earth metal salts, particularly calcium or magnesium, and salts with suitable organic bases such as lower alkylamines (methylamine, ethylamine, cyclohexylamine, and the like) or with substituted lower alkylamines (e.g. hydroxyl-substituted alkylamines such as diethanolamine, triethanolamine or tris(hydroxymethyl)-aminomethane), or with bases such as piperidine or morpholine.

As used herein, the term "prodrug" refers to a compound that is converted to a therapeutically active compound after administration, and the term should be interpreted as broadly herein as is generally understood in the art. Generally, but not necessarily, a prodrug is inactive or less active than the therapeutically active compound to which it is converted. For example, a methyl ester can be converted to a free carboxylic acid in vivo via the action of non-specific serum esterases.

As used herein, the term "stereoisomer" refers to a compound which has the identical chemical constitution but differs with regard to the arrangement of the atoms or groups in space.

It is to be understood that the compounds provided herein may contain chiral centers. Such chiral centers may be of either the (R) or (S) configuration or may be a mixture thereof. Thus, the compounds provided herein may be enantiomerically pure, or be stereoisomeric or diastereomeric mixtures. It is to be understood that the chiral centers of the compounds provided herein may undergo epimerization in vivo. As such, one of skill in the art will recognize that administration of a compound in its (R) form is equivalent, for compounds that undergo epimerization in vivo, to administration of the compound in its (S) form.

Compounds of the disclosure, such as those disclosed according to the various embodiments, and novel agents referred to herein, may exist as stereoisomers and/or geometric isomers—e.g. they may possess one or more asymmetric and/or geometric centers and so may exist in two or more stereoisomeric and/or geometric forms. Contemplated herein is the use of all the individual stereoisomers and geometric isomers of those inhibitor agents, and mixtures thereof. The terms used in the claims encompass these forms, provided said forms retain the appropriate functional activity (though not necessarily to the same degree).

Compounds of the disclosure also include all suitable isotopic variations of the agent or pharmaceutically acceptable salts thereof. An isotopic variation of an anti-malarial agent or a pharmaceutically acceptable salt thereof is defined as one in which at least one atom is replaced by an atom having the same atomic number but an atomic mass different from the atomic mass usually found in nature. Examples of isotopes that can be incorporated into the agent and pharmaceutically acceptable salts thereof include isotopes of hydrogen, carbon, nitrogen, oxygen, phosphorus, sulphur, fluorine and chlorine such as 2H, 3H, 13C, 14C, 15N, 17O, 18O, 31P, 32P, 35S, 18F and 36Cl, respectively. Certain isotopic variations of the agent and pharmaceutically acceptable salts thereof, for example, those in which a radioactive isotope such as 3H or 14C is incorporated, are useful in drug and/or substrate tissue distribution studies. Tritiated, i.e., 3H, and carbon-14, i.e., 14C, isotopes are particularly preferred for their ease of preparation and detectability. Further, substitution with isotopes such as deuterium, i.e., 2H, may afford certain therapeutic advantages resulting from greater metabolic stability, for example, increased in vivo half-life or reduced dosage requirements and hence may be preferred in some circumstances. Isotopic variations of the anti-malarial agents and pharmaceutically acceptable salts thereof of this disclosure can generally be prepared by conventional procedures using appropriate isotopic variations of suitable reagents.

According to various embodiments, the compounds of the disclosure and novel agents referred to herein, may also include solvate forms of the compounds. The terms used in the claims encompass these forms.

The compounds of the disclosure and novel agents referred to herein, also include their various crystalline forms, polymorphic forms and (an)hydrous forms. It is well established within the pharmaceutical industry that chemical compounds may be isolated in any of such forms by slightly varying the method of purification and or isolation form the solvents used in the synthetic preparation of such compounds.

Also falling within the scope of this invention are the in vivo metabolic products of the anti-malarial compounds described herein. A "metabolite" is a pharmacologically active product produced through metabolism in the body of a specified compound or salt thereof. Such products can result, for example, from the oxidation, reduction, hydrolysis, amidation, deamidation, esterification, deesterification, enzymatic cleavage, and the like, of the administered compound. Accordingly, the invention includes metabolites of the compounds according to the various embodiments, including compounds produced by a process comprising contacting a compound of this invention with a mammal for a period of time sufficient to yield a metabolic product thereof.

In addition to the active ingredients, these pharmaceutical compositions can contain suitable pharmaceutically acceptable carriers comprising excipients and auxiliaries, which facilitate processing of the active compounds into preparations which can be used pharmaceutically. Pharmaceutical compositions of the invention can be administered by any number of routes including, but not limited to, oral, intravenous, intramuscular, intra-arterial, intramedullary, intrathecal, intraventricular, transdermal, subcutaneous, intraperitoneal, intranasal, parenteral, topical, sublingual, or rectal means. Pharmaceutical compositions for oral administration can be formulated using pharmaceutically acceptable carriers well known in the art in dosages suitable for oral administration. Such carriers enable the pharmaceutical compositions to be formulated as tablets, pills, dragees, capsules, liquids, gels, syrups, slurries, suspensions, and the like, for ingestion by the patient.

Pharmaceutical preparations for oral use can be obtained through combination of active compounds with solid excipient, optionally grinding a resulting mixture, and processing the mixture of granules, after adding suitable auxiliaries, if desired, to obtain tablets or dragee cores. Suitable excipients are carbohydrate or protein fillers, such as sugars, including lactose, sucrose, mannitol, or sorbitol; starch from corn, wheat, rice, potato, or other plants; cellulose, such as methyl cellulose, hydroxypropylmethylcellulose, or sodium carboxymethylcellulose; gums including arabic and tragacanth; and proteins such as gelatin and collagen. If desired, disintegrating or solubilizing agents can be added, such as the cross-linked polyvinyl pyrrolidone, agar, alginic acid, or a salt thereof, such as sodium alginate.

Dragée cores can be used in conjunction with suitable coatings, such as concentrated sugar solutions, which also can contain gum arabic, talc, polyvinylpyrrolidone, carbopol gel, polyethylene glycol, and/or titanium dioxide, lacquer solutions, and suitable organic solvents or solvent mixtures. Dyestuffs or pigments can be added to the tablets or dragee coatings for product identification or to characterize the quantity of active compound, i.e., dosage. Pharmaceutical preparations which may be used orally include push fit capsules made of gelatin, as well as soft, sealed capsules made of gelatin and a coating, such as glycerol or sorbitol. Push fit capsules can contain active ingredients mixed with a filler or binders, such as lactose or starches, lubricants, such as talc or magnesium stearate, and, optionally, stabilizers. In soft capsules, the active compounds can be dissolved or suspended in suitable liquids, such as fatty oils, liquid, or liquid polyethylene glycol with or without stabilizers.

Pharmaceutical formulations suitable for parenteral administration may be formulated in aqueous solutions, preferably in physiologically compatible buffers such as Hanks' solution, Ringer's solution, or physiologically buffered saline. Aqueous injection suspensions can contain substances which increase the viscosity of the suspension, such as sodium carboxymethyl cellulose, sorbitol, or dextran. Additionally, suspensions of the active compounds can be prepared as appropriate oily injection suspensions. Suitable lipophilic solvents or vehicles include fatty oils such as sesame oil, or synthetic fatty acid esters, such as ethyl oleate or triglycerides, or liposomes. Non-lipid polycationic amino polymers also can be used for delivery. Optionally, the suspension also may contain suitable stabilizers or agents which increase the solubility of the compounds to allow for the preparation of highly concentrated solutions. For topical or nasal administration, penetrants appropriate to the particular barrier to be permeated are used in the formulation. Such penetrants are generally known in the art.

The pharmaceutical compositions of the present invention can be manufactured in a manner that is known in the art, e.g., by means of conventional mixing, dissolving, granulating, dragée making, levigating, emulsifying, encapsulating, entrapping, or lyophilizing processes. The pharmaceutical composition can be provided as a salt and can be formed with many acids, including but not limited to, hydrochloric, sulfuric, acetic, lactic, tartaric, malic, succinic, etc. Alternatively, salts can be formed with many amine motifs such as primary, secondary and tertiary amines or even the native polyamines themselves. Salts tend to be more soluble in aqueous or other protonic solvents than are the corresponding free base or free acid forms.

According to various embodiments, one or more compounds according to various embodiments may be delivered using one or more liposomes. Preferably, the liposome is stable in the animal into which it has been administered for at least about 30 minutes, more preferably for at least about 1 hour, and even more preferably for at least about 24 hours. A liposome comprises a lipid composition that is capable of targeting a reagent to a particular site in an animal, such as a human. Preferably, the lipid composition of the liposome is capable of targeting to a specific organ of an animal, such as the lung, liver, spleen, pancreas, heart brain, lymph nodes, and skin.

A liposome useful in the present invention comprises a lipid composition that is capable of fusing with the plasma membrane of the targeted cell to deliver its contents to the cell. Preferably, a liposome is between about 100 and 500 nm, more preferably between about 150 and 450 nm, and even more preferably between about 200 and 400 nm in diameter.

Suitable liposomes for use in the present invention include those liposomes standardly used in, for example, gene delivery methods known to those of skill in the art. More preferred liposomes include liposomes having a polycationic lipid composition and/or liposomes having a cholesterol backbone conjugated to polyethylene glycol. Optionally, a liposome comprises a compound capable of targeting the liposome to a particular cell type, such as a cell-specific ligand exposed on the outer surface of the liposome.

According to various embodiments, any of the pharmaceutical compositions of the invention can be administered in combination with other appropriate therapeutic agents. Selection of the appropriate agents for use in combination therapy can be made by one of ordinary skill in the art, according to conventional pharmaceutical principles. The combination of therapeutic agents can act synergistically to effect the treatment or prevention of the various disorders described above. Using this approach, one may be able to achieve therapeutic efficacy with lower dosages of each agent, thus reducing the potential for adverse side effects. Any of the therapeutic methods described above can be applied to any subject in need of such therapy, including, for example, mammals such as dogs, cats, cows, horses, rabbits, sheep, monkeys, and most preferably, humans.

The following abbreviations may be used herein: Pf, *Plasmodium falciparum*; CQ, Chloroquine; ACTs, artemisinin-based combination therapies; DV, digestive vacuole; PfCRT, *Plasmodium falciparum* chloroquine resistance transporter; DHA, dihydroartemisinin; PPA, polyphosphoric acid; p-Ts$NH_2$, p-toluenesulfonamide; and po, per oral.

General Discussion

Various embodiments relate to new compounds with significantly enhanced activity over Formula 1 towards *P. falciparum* in vitro and murine *P. berghei* ANKA in vivo. These new compounds hold excellent potential for treating malaria.

The new compounds according to various embodiments are similar to compounds according to Formula 1, but with many structural variations. Formula 3 summarizes points of structural variation.

Formula 3

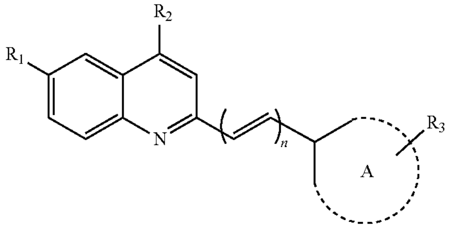

Development of various embodiments involved investigating the relationship between $R_1$ and $R_2$ groups located at position C6 and C4 respectively, as well as the absence of styryl moiety or double bond between quinoline scaffold and $R_3$-substituted aromatic or heterocyclic ring A. The antimalarial activity of various styrylquinolines was investigated and surprising results were achieved.

It was unexpectedly discovered that introducing a chlorine (Cl) atom as the $R_1$ moiety increased the potency. It was unexpectedly discovered that the pattern of amino groups at the $R_2$ moiety significantly affects the antimalarial activity. It was unexpectedly discovered that the absence of an arylvinyl moiety at ring A results in diminished antimalarial activity. It was unexpectedly discovered that having an aromatic fragment at ring A plays an important role in the antimalaria potency. It was unexpectedly discovered that replacement of phenyl by cyclohexyl, naphthyl and heterocyclics at ring A leads to decreased activity. It was unexpectedly discovered that having an electron-donating group as the $R_3$ moiety decreases the potency. It was unexpectedly discovered that ortho positional substituents as the $R_3$ moiety is detrimental to the antimalarial potency. It was unexpectedly discovered that having multiple fluoro-containing groups as the $R_3$ moieties do not show synergistic effects. Finally, it was unexpectedly discovered that the double bond (n>0) between the quinoline scaffold and the aromatic ring A is required to provide the desired antimalarial activity.

Formula 2 provides a simplified version of Formula 3, with several of the moieties specified to focus on the most important embodiments. The R-groups have been renumbered in Formula 2 for simplicity to allow Formula 2 to stand alone without reference to Formula 3.

Formula 2

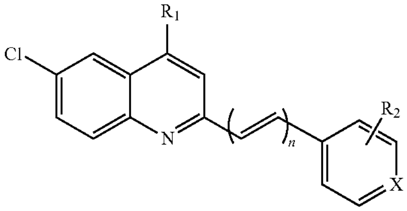

Referring to Formula 2, according to various embodiments:

n may be 1 or 2;

X may be C or N;

$R_1$ may be a moiety comprising a secondary amine and a tertiary amine joined by a $C_2$ to $C_4$ alkyl chain; and $R_2$ may be $CF_3$, F, or H and multiple $R_2$ groups may be present.

Still referring to Formula 2, according to various embodiments, $R_1$ may be any of the following moieties, in which the wavy line indicates the bond via which the $R_1$ group is attached to the quinoline scaffold:

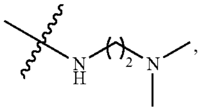

, 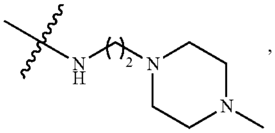

, or

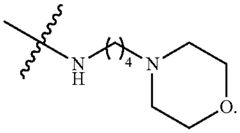

In this work, intensive SAR studies were performed around a quinoline scaffold leading to the generation of 6-chloro-arylvinylquinolines. The SAR trends were summarized in FIG. 8. Many promising arylethenylaminoquinolines exhibited more potent antimalarial activity than the positive controls (CQ and a compound according to Formula 1), among which compounds 24, 29, 31, 86, 92 and 93 were highly active ($EC_{50}$≤15 nM). The inhibitory effects of all compounds tested toward CQ-resistant strain were much stronger than that toward CQ-susceptible strain (RI<1), suggesting no cross-resistance induced by this chemotype. Various embodiments exhibit good potency, selectivity and physicochemical properties.

The most promising compound 24 ($EC_{50}$=10.9±1.9 nM against Dd2 strain; $t_{1/2}$=104.2 min), a fast-acting parasitocidal agent with robust blood and gametocyte stage activity, displayed stage specific action at the trophozoite phase in Pf asexual life cycle. Very importantly, 24 displayed remarkable efficacy in the rodent malaria model, resulting in 100% reduction of parasitemia in 5/5 mice at 100 mg/kg, p.o. and 3/4 mice at 25 mg/kg, po, without apparent signs of toxicity. Additionally, compound 24 showed weaker inhibitory activity towards β-hematin formation as compared to CQ, indicating that the potent antimalarial activity of 24 might be associated with other mode of actions. The 6-chloro-arylvinylquinolines, corresponding to compound 24, according to various embodiments, may use for various new antimalarial applications.

According to various embodiments, the compound may be Compound 24:

Compound 24

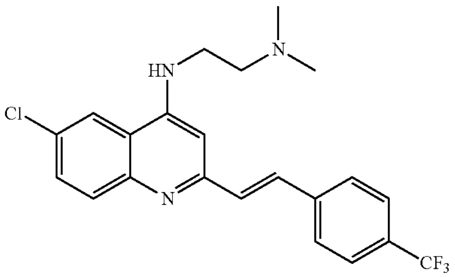

Compound 24 exhibited various unexpected benefits compared to the compound according to Formula 1.

The compounds according to Formula 1 may have Pf Asexual $EC_{50}$=67.0±8.0 nM (Dd2 strain); SI=193, RI=0.6; Microsomal stability (MLM): $t_{1/2}$=41.5 min; and in vivo efficacy=100 mg/kg twice daily, po.

Compound 24 may have Pf Asexual $EC_{50}$=10.9±1.9 nM (Dd2 strain); SI=1031; RI=0.6; Pf Gametocyte $EC_{50}$=471.5±18.4 nM (early stage); $EC_{50}$=393.6±99.4 nM (late stage); Microsomal stability (MLM): $t_{1/2}$=104.2 min; and in vivo efficacy=25 mg/kg once daily, po.

EXAMPLES

Introduction

The following examples are put forth to provide those of ordinary skill in the art with a complete disclosure and description of how to perform the methods, how to make, and how to use the compositions and compounds disclosed and claimed herein. Efforts have been made to ensure accuracy with respect to numbers (e.g., amounts, temperature, etc.), but some errors and deviations should be accounted for.

A set of 104 new styrylquinoline derivatives were synthesized and investigated for in vitro their antimalarial activity. To test antimalarial activities, different dilutions of compounds were added to *P. falciparum* culture. Following 72 h incubation at 37° C. in an atmosphere containing 5% $CO_2$, the inhibitory property of the compounds were determined by SYBR Green I fluorescence assay. Meanwhile, SARs studies were conducted. Most of them displayed better efficacy than positive controls, among which, compounds 24, 29, 31, 76, 80 and 81 were highly active ($IC_{50}$≤15 nM).

Selectivity of compounds were determined by cytoxicity assay using MTS [(3-(4,5-dimethylthiazol-2-yl)-5-(3-carboxymethoxyphenyl)-2-(4-sulfophenyl)-2H-tetrazolium) in human hepatocytes. The metabolic stability of compounds was determined in mouse liver microsomes using an NADPH-regenerating system. The aqueous solubility at pH 7.4 was determined by UV-visible absorption based method. The permeability was assessed by the in vitro double-sink parallel artificial membrane permeability assay 52 that is a model for the passive transport from the gastrointestinal tract into the blood stream.

In each example, the constituents are relabeled based on the set of compounds synthesized and tested in the example. To ensure clarity, the specific structure tested is represented in association with tables providing test results. The compound numbers (e.g., Compound 24) assigned to each tested compound are used consistently throughout.

The purpose of the following examples is not to limit the scope of the various embodiments, but merely to provide examples illustrating specific embodiments.

Example 1

A purpose of this example was to demonstrate the syntheses of Compounds 8-37 (Scheme 1 and Table 1) started from commercially available anilines 1a-d. The reaction of anilines 1a with ethyl acetoacetate 2 in the presence of acetic acid afforded an imine intermediate, which was converted to hydroxyquinoline 3a at elevated temperature. Alternatively, hydroxyquinolines 3a-d were synthesized by treatment of aniline 1a-d with 2 in the presence of PPA. Chlorination of hydroxyquinolines 3a-d with phosphorus oxychloride gave 4-chloroquinolines 4a-d in quantitative yields, which were then reacted with neat N,N-dimethylaminoalkylamine 5 via nucleophilic substitution to produce aminoquinolines 6a-6e in excellent yields. Subsequent olefination of 6a-6e with appropriate aromatic aldehydes 7a-1 using p-$TsNH_2$ as a catalyst were carried out in xylene to afford (E)-styrylquinolines 8-37.

Scheme 1 is an example according to various embodiments illustrating the synthesis of 6-substituted 2-styrylquinoline derivatives, corresponding to compounds 8-37$^{\alpha}$.

Scheme 1

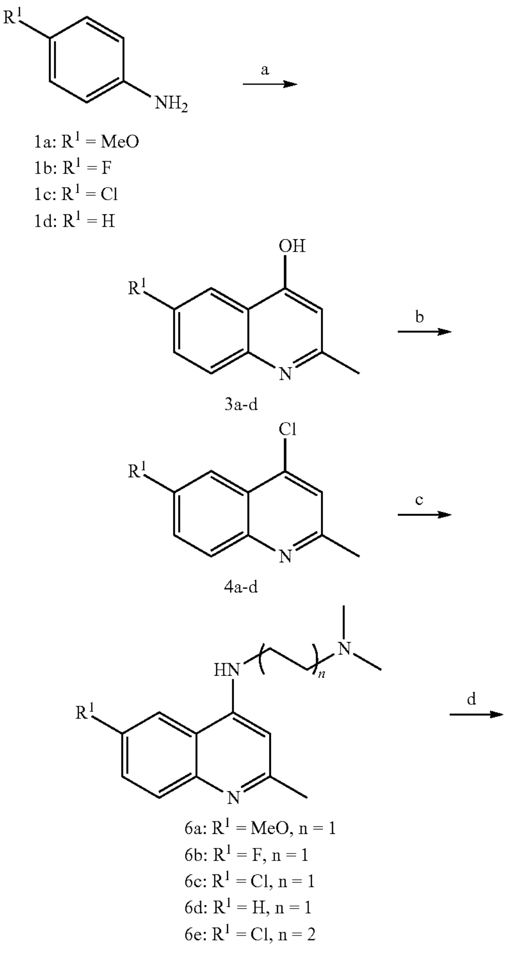

-continued

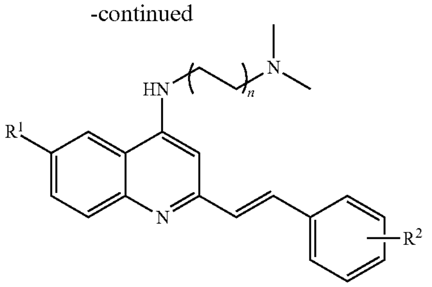

8-37

$R^2$ = H (7a), 4/2/3-$NO_2$ (7b-d), 4-OMe (7e), 3,4-diOMe (7f), 3 ,4, 5, -triOMe (7g), 4-F (7h), 4-$CF_3$ (7i), 4-N,N-dimethylamino (7j), 2/3-F (7k-l)

[a]Reagents and conditions: a) method A for 3a: i. aniline, ethyl acetoacetate 2, acetic acid, anhydrous magnesium sulfate, ethanol, 90° C., 6 h; ii. Dowtherm, 270° C., 30 min, 43% for 2 steps; method B: aniline, ethyl acetoacetate 2, PPA, 150° C., 2 h, 57-68%; b) phosphorus oxychloride, 105° C., 2 h, 85-90%; c) N,N-dimethylaminoalkylamine 5, 130° C., 24 h, 87-93%; d) aromatic aldehydes 7a-l, p-$TsNH_2$, xylene, 130° C., 12 h, 60-89%.

In Vitro Antiplasmodial Activity and Cytotoxicity

The SAR studies were focused on improving the in vitro activity of 2-arylvinylquinolines against the CQ-resistant Pf Dd2 strain. A series of styrylquinoline analogues 8-34 bearing various C6 substituents ($R^1$) and benzenoid substituents ($R^2$) were evaluated for their in vitro activity toward Dd2 strain (Table 1).

In the C6-methoxy series, compound 9 ($R^2$=4-$NO_2$, $EC_{50}$=28.6±0.9 nM) exhibited slightly higher inhibitory activity than the unsubstituted compound 8 ($R^2$=H, $EC_{50}$=41.2±5.3 nM). Shifting the nitro group in compound 9 from para-position to ortho- or meta-position led to decreased activity, as seen with compound 10 ($EC_{50}$=56.3±8.1 nM) and 11 ($EC_{50}$=49.5±4.0 nM). Replacement of the nitro group with 4-methoxy, 3,4-dimethoxy and 3,4,5-trimethoxy groups afforded compounds 12-14, giving rise to the decreased activity.

The introduction of a fluorine atom at C-6 position of quinoline scaffold generally resulted in improved antimalarial activity over the corresponding methoxylated analogues. For instance, compound 16 ($R^2$=H, $EC_{50}$=21.0±2.1 nM) and compound 21 ($R^2$=3,4,5-trimethoxy, $EC_{50}$=38.6±1.8 nM) showed almost 2 times more potent activity than the counterparts 8 and 14. Another noteworthy observation was that fluorinated analogue 20 with 3,4-dimethoxy group exhibited approximately 4.5-fold improved activity as compared to compound 13.

Substitution of the fluorine atom by a chlorine atom led to further enhancement of the antimalarial activity. C6-chloro styrylquinolines bearing a fluoro or trifluoromethyl group on the benzene ring showed potent activity toward Dd2 strain. Among these analogues, compound 29 ($R^2$=4-F) was the most active one with an $EC_{50}$ value of 4.8±2.0 nM, which was almost 6-fold and 14-fold more potent than Artemisinin and a compound according to Formula 1, respectively. Compared with compound 29, compound 24 and 31 demonstrated slightly declined inhibitory activity with $EC_{50}$ values of 10.9±1.9 and 5.9±1.4 nM. However, altering the fluorine atom of compound 29 from para position to ortho position induced 5-fold decrease in activity as observed with compound 30 ($EC_{50}$=26.0±0.9 nM). For all styrylquinolines ($R^1$=—OMe, —F and —Cl), the introduction of electron-rich groups ($R^2$) turned out to be detrimental to the antiplasmodial potency, e.g. compounds 12-14, 19-21 and 25-28 were less active relative to their analogues ($R^2$=H and 4-$NO_2$).

Removal of C6-substituent ($R^1$=H) caused the significant drop in the antimalarial activity. For example, compounds 32 ($R^1$=H, $EC_{50}$=80.7±22.4 nM) exhibited much lower activity than the corresponding analogues 8 ($R^1$=MeO), 16 ($R^1$=F) and 22 ($R^1$=Cl). Therefore, the general trend of the substituents at the C6 position in the order of improved potency is H<OMe<F<Cl.

The spacing parameter for the C4 amino side-chain of styrylquinolines was also investigated. As shown in Table 1, significant loss of potency was observed for the compounds containing dimethylaminobutyl group. It appeared that, for styrylquinolines, dimethylaminoethylamine was a superior side-chain to dimethylaminobutylamine.

Table 1 shows antimalarial activity of targets according to Formula 4 against CQ-resistant (Dd2) strain. The targets had structures according to Formula 4, with moieties as shown in Table 1.

Formula 4

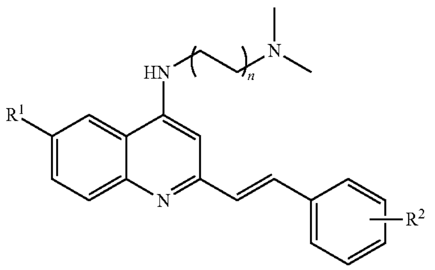

It should be noted that multiple $R^2$ groups may be present. For example, according to Compound 21, three $R^2$ groups are present.

TABLE 1

| Compd. | $R^1$ | n | $R^2$ | EC50 (nmol) |
|---|---|---|---|---|
| 8 | MeO | 1 | H | 41.2 ± 5.3 |
| 9 | MeO | 1 | 4-NO2 | 28.6 ± 0.9 |
| 10 | MeO | 1 | 2-NO2 | 56.3 ± 8.1 |
| 11 | MeO | 1 | 3-NO2 | 49.5 ± 4.0 |
| 12 | MeO | 1 | 4-OMe | 43.6 ± 2.0 |
| 13 | MeO | 1 | 3,4-diOMe | 187.3 ± 13.6 |
| 14 | MeO | 1 | 3,4,5-triOMe | 74.2 ± 8.8 |
| 15 | MeO | 1 | 4-F | 32.9 ± 5.1 |
| 16 | F | 1 | H | 21.0 ± 2.1 |
| 17 | F | 1 | 4-NO2 | 30.9 ± 5.9 |
| 18 | F | 1 | 4-F | 30.9 ± 5.5 |
| 19 | F | 1 | 4-OMe | 37.8 ± 8.7 |
| 20 | F | 1 | 3,4-diOMe | 41.1 ± 0.6 |
| 21 | F | 1 | 3,4,5-triOMe | 38.6 ± 1.8 |
| 22 | Cl | 1 | H | 22.4 ± 2.0 |
| 23 | Cl | 1 | 4-NO2 | 28.7 ± 3.8 |
| 24 | Cl | 1 | 4-CF3 | 10.9 ± 1.9 |
| 25 | Cl | 1 | 4-OMe | 34.8 ± 7.9 |
| 26 | Cl | 1 | 3,4-diOMe | 38.9 ± 7.8 |
| 27 | Cl | 1 | 3,4,5-triOMe | 44.4 ± 3.6 |
| 28 | Cl | 1 | 4-N,N-dimethylamino | 88.3 ± 2.2 |
| 29 | Cl | 1 | 4-F | 4.8 ± 2.0 |
| 30 | Cl | 1 | 2-F | 26.0 ± 0.9 |
| 31 | Cl | 1 | 3-F | 5.9 ± 1.4 |
| 32 | H | 1 | H | 80.7 ± 22.4 |
| 33 | H | 1 | 4-NO2 | 47.9 ± 9.5 |

TABLE 1-continued

| Compd. | $R^1$ | n | $R^2$ | EC50 (nmol) |
|---|---|---|---|---|
| 34 | H | 1 | 4-F | 25.5 ± 7.1 |
| 35 | Cl | 2 | H | 68.0 ± 9.0 |
| 36 | Cl | 2 | 4-NO2 | 52.5 ± 2.0 |
| 37 | Cl | 2 | 4-F | 51.2 ± 1.6 |
| Compound according to Formula 1 | | | | 67.0 ± 8.0 |
| CQ | | | | 174.0 ± 15.5 |
| Artemisinin | | | | 28.0 ± 6.0 a |

a Values reported from another study.

Example 2

A purpose of this example was to demonstrate the effect of heterocycles and carbocycles other than benzenoid on the antimalarial potency, 2-arylalkenylquinolines 39-57 (Scheme 2 and Table 2) were synthesized from 2-methylquinolines 6a-c, following the same synthetic sequence as shown for styrylquinolines 8-37.

Scheme 2 is an example according to various embodiments illustrating the synthesis of 6-substituted 2-arylvinylquinolines 39-57$^{\alpha}$.

Scheme 2

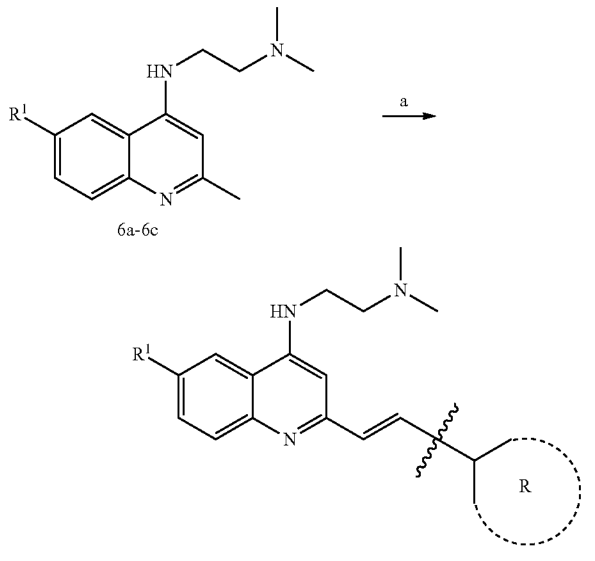

6a-6c 39-57

R =

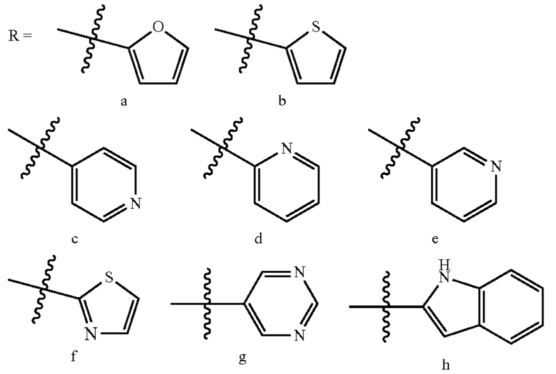

a b c d e f g h

-continued

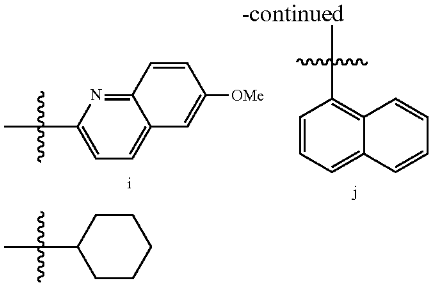

i j k $^{\alpha}$Reagents and conditions: a) p-TsNH$_2$, aldehydes 38a-k, xylene, 130° C., 12 h, 48-86%.

In Vitro Antiplasmodial Activity and Cytotoxicity

The SAR studies were focused on improving the in vitro activity of 2-arylvinylquinolines against the CQ-resistant Pf Dd2 strain. Having determined the impacts of dimethylaminoalkyl and halogen substituents on the styrylquinoline scaffold on the antimalarial activity, the experiments described in this example sought to test whether the replacement of phenyl ring (R) with heterocycles and non-benzenoid carbocycles affect the inhibitory activity against Dd2 strain (Table 2). Substitutions of the benzenoid motif by five-membered aromatic heterocycles including furan (compounds 39, 44 and 47), thiophene (compounds 40, 45 and 48) and thiazole (compound 49) led to the reduced antimalarial activity. However, replacement of the phenyl group with a 4-pyridyl group (compounds 41, 46 and 50) retained potent antimalarial potency. Importantly, the position of nitrogen atom appeared to influence the antimalarial activity significantly. For instance, 4-pyridylvinylquinoline 50 was approximately 2 times more potent than compound 51 bearing 2-pyridylvinyl group and this manifestation became more evident for methoxylated pyridylvinylquinolines since the activity difference was up to 30 times, e.g. compound 41 (R=4-pyridyl, $EC_{50}$=33.6±5.8 nM) and 42 (R=2-pyridyl, $EC_{50}$=1032.8±232.9 nM).

Chlorinated vinylquinolines were found to be more potent than the corresponding fluorinated and methoxylated analogues. For instance, compound 47 ($R^1$=MeO, $EC_{50}$=37.0±4.3 nM) showed 2 times higher activity than compound 39 ($R^1$=MeO, $EC_{50}$=88.7±2.3 nM) and 44 ($R^1$=MeO, $EC_{50}$=82.6±9.4 nM). Accordingly, this work further confirmed previous conclusions that the chlorine atom at C-6 position of the styrylquinoline scaffold was superior to fluorine atom and methoxy substituent for the antimalarial potency.

In addition, it was found that replacement of pyridine by other heterocycles such as pyrimidine, indole and quinoline resulted in the marked loss of potencies, as seen with the corresponding arylvinylquinolines 53 ($EC_{50}$=155.0±11.6 nM), 54 ($EC_{50}$=95.9±6.7 nM) and 55 ($EC_{50}$=281.3±40.3 nM). Unfortunately, the search for active compounds by incorporating carbocycles, such as naphthalene and saturated cyclohexane, to the vinylquinoline scaffold failed to provide any analogue that was more potent than the phenyl counterpart 22.

Table 2 shows antimalarial activity of targets according to Formula 5 against CQ-resistant (Dd2) strain. The targets had structures according to Formula 5, with moieties as shown in Table 2.

Formula 5

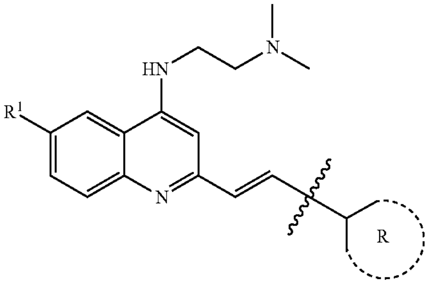

TABLE 2

| Compd. | R[1] | R | EC50 (nmol) |
|---|---|---|---|
| 39 | MeO | 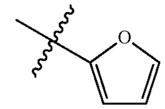 [SMILES: *c1ccco1] | 88.7 ± 2.3 |
| 40 | MeO | 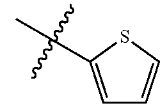 [SMILES: *c1cccs1] | 80.0 ± 7.0 |
| 41 | MeO | 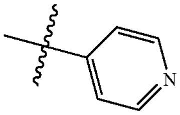 [SMILES: *c1ccncc1] | 38.8 ± 4.7 |
| 42 | MeO | 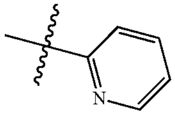 | 1032.8 ± 232.9 |
| 43 | MeO | 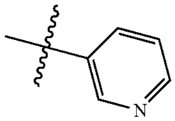 | 71.0 ± 27.5 |
| 44 | F | 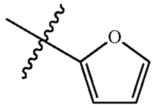 [SMILES: *c1ccco1] | 82.6 ± 9.4 |
| 45 | F | 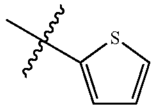 [SMILES: *c1cccs1] | 110.9 ± 29.1 |
| 46 | F | 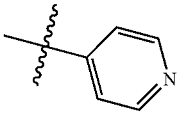 [SMILES: *c1ccncc1] | 36.1 ± 2.1 |
| 47 | Cl | 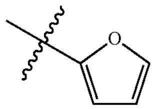 [SMILES: *c1ccco1] | 37.0 ± 4.3 |

TABLE 2-continued

| Compd. | R[1] | R | EC50 (nmol) |
|---|---|---|---|
| 48 | Cl | 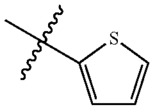 [SMILES: *c1cccs1] | 29.7 ± 4.6 |
| 49 | Cl | 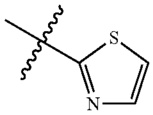 [SMILES: *c1nccs1] | 239.7 ± 30.6 |
| 50 | Cl | 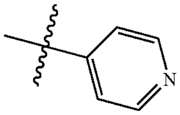 [SMILES: *c1ccncc1] | 28.8 ± 5.0 |
| 51 | Cl | 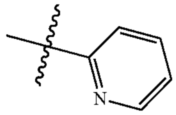 [SMILES: *c1ccccn1] | 67.5 ± 1.9 |
| 52 | Cl | 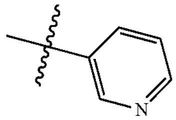 [SMILES: *c1cccnc1] | 33.6 ± 5.8 |
| 53 | Cl | 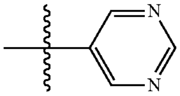 [SMILES: *c1cncnc1] | 155.0 ± 11.6 |
| 54 | Cl | 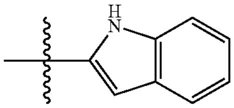 [SMILES: *c1cc2ccccc2[nH]1] | 95.9 ± 6.7 |
| 55 | Cl | 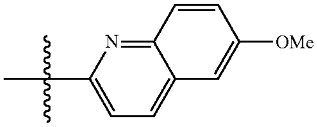 [SMILES: *c1ccc2cc(OC)ccc2n1] | 281.3 ± 40.3 |
| 56 | Cl | 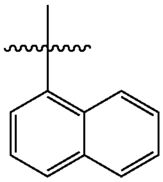 [SMILES: *c1cccc2ccccc12] | 373.0 ± 19.0 |
| 57 | Cl | 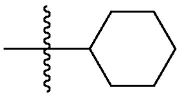 [SMILES: *C1CCCCC1] | 394.0 ± 40.0 |

Example 3

A purpose of this example was to demonstrate the influence of the double bond between the quinoline core and the aromatic ring on the antimalarial activity, 2-pyridylethylquinolines 58 and 59 were prepared in good yields (Scheme 3 and Table 3) through the reduction of 2-pyridylvinylquinolines (41 and 50) with hydrazine hydrate at 80° C., respectively.

Scheme 3 is an example according to various embodiments illustrating the synthesis of 6-substituted 2-alkylquinolines 58-59[α].

Scheme 3

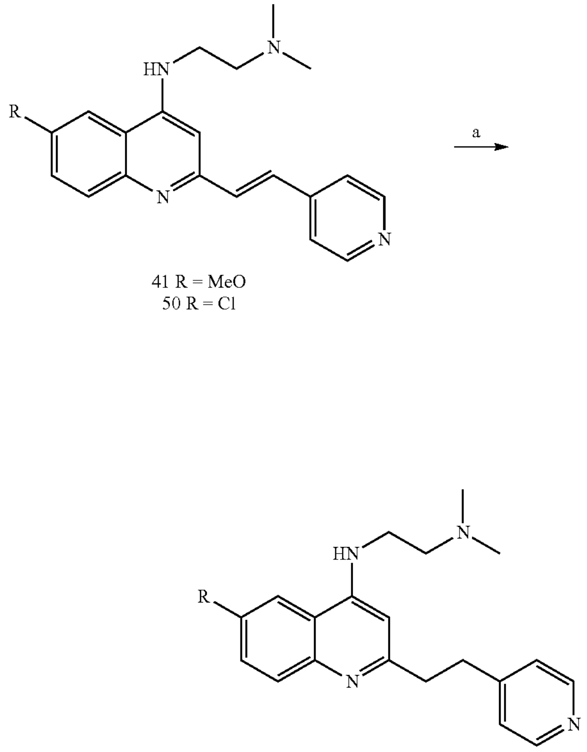

41 R = MeO
50 R = Cl

58 R = MeO
59 R = Cl

[α]Reagents and conditions: a) hydrazine hydrate, EtOH, 80° C., 36 h, 81-83% yield.

In Vitro Antiplasmodial Activity and Cytotoxicity

The SAR studies were focused on improving the in vitro activity of 2-arylvinylquinolines against the CQ-resistant Pf Dd2 strain. Compared to 4-aminoquinolines, e.g. CQ, a unique feature of the lead compounds, according to various embodiments, is the vinyl group that bridges the quinoline core and the aromatic ring. In this series, it was intended to assess the impacts of the double bond on antimalarial activity. As illustrated in Table 3, in the absence of arylvinyl group, aminoquinolines 6a, 6c and 6e were inactive toward Dd2 strain. Even with an aromatic group, the saturated analogues showed almost an order of magnitude weaker activity than the vinyl analogues, as demonstrated by pyridylvinylquinoline 58 ($EC_{50}$=708.7±58.2 nM) vs 41 ($EC_{50}$=38.8±4.7 nM) and pyridylvinylquinolines 59 ($EC_{50}$=259.0±15.5 nM) vs 50 ($EC_{50}$=28.8±5.0 nM). Therefore, these data confirmed that the absence of the 2-arylvinyl moiety severely diminished the antimalarial activity. Meanwhile, these data suggested the possible interactions between the arylvinyl motif and the molecular target(s).

Table 3 shows antimalarial activity of targets according to Formula 6 against CQ-resistant (Dd2) strain. The targets had structures according to Formula 6, with moieties as shown in Table 3.

Formula 6

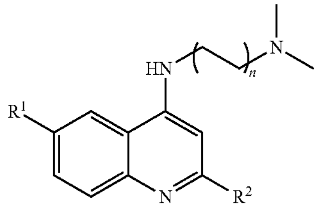

TABLE 3

| Compd. | $R^1$ | n | $R^2$ | EC50 (nmol) |
|---|---|---|---|---|
| 6a | MeO | 1 | Me | 5516.0 ± 571.3 |
| 6c | Cl | 1 | Me | 731.6 ± 107.1 |
| 6e | Cl | 2 | Me | 1245.0 ± 139.2 |
| 41 | MeO | 1 | 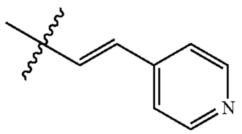 [SMILES: */C=C/c1ccncc1] | 38.8 ± 4.7 |
| 58 | MeO | 1 | 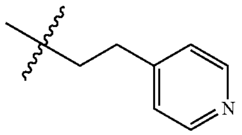 [SMILES: *CCc1ccncc1] | 708.7 ± 58.2 |
| 50 | Cl | 1 | 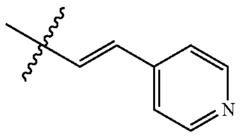 [SMILES: */C=C/c1ccncc1] | 28.8 ± 5.0 |
| 59 | Cl | 1 | 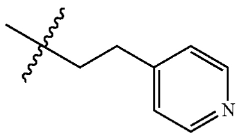 [SMILES: *CCc1ccncc1] | 259.0 ± 15.5 |

Example 4

A purpose of this example was to demonstrate the effect of C4-amino group on the arylvinylquinoline scaffold on the antimalarial potency. To this end, arylvinylquinoline derivatives 62-72, 81-87 and 90-96 were synthesized (Table 4). The synthetic route of target compounds 62-72 was depicted in Scheme 4, using a similar chemistry as described in Scheme 1. A growing number of studies have demonstrated that isonitrile group displays good antimalarial activity, and thus compound 64 was synthesized for the antimalarial evaluation. Initially, a direct olefination reaction was adopted to construct the arylvinylquinoline motif, but no discernable Compound 64 was detected.

Scheme 4 is an example according to various embodiments illustrating the synthesis of 4-substituted-arylvinylquinolines 62-72[α].

Scheme 4

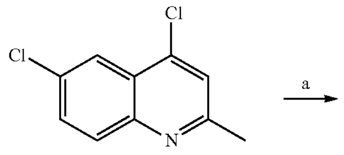

4c

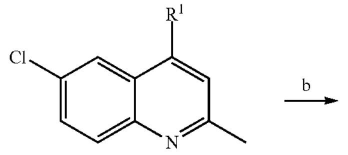

61a-f

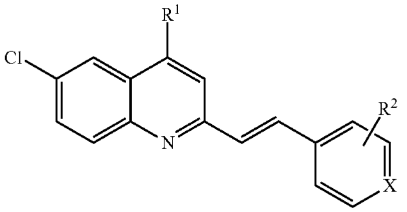

62-72

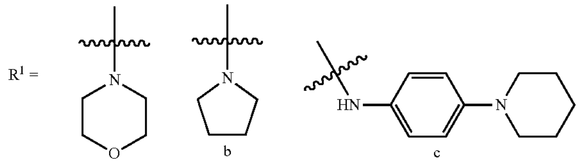

a b c

-continued

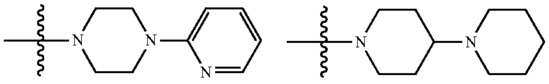

d e

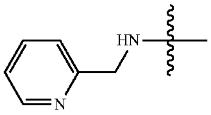

f $R^2$ = 4F and H; X = C or N

[α]Reagents and conditions: a) amines 60a-f, 130° C., EtOH, 12 h, 73-92%; b) aldehydes 7a, 7h or 38c, p-TsNH$_2$, xylene, 130° C., 12 h, 48-89%.

As discussed with respect to Scheme 4, a direct olefination reaction was adopted to construct the arylvinylquinoline motif, but no discernable Compound 64 was detected. An alternative synthetic route was adopted to prepare isonitrile 64 (Scheme 5). In detail, benzyl bromide 73 reacted with stoichiometric amount of triethylphosphite to give phosphonate 74 via an Arbuzov reaction, which was then converted to amine 75 by reduction of the nitro group. Isonitrile 76 was obtained by treatment of amine 75 with chloroform in the presence of a base. Subsequently, aldehyde 77, derived from selenium dioxide oxidation of 2-methylquinoline 61a, reacted with phosphonate 76 to afford isonitrile 64 in moderate yield via an Horner-Wadsworth-Emmons reaction.

Scheme 5 is an example according to various embodiments illustrating the synthesis of isonitrile styrylquinoline 64[α].

Scheme 5

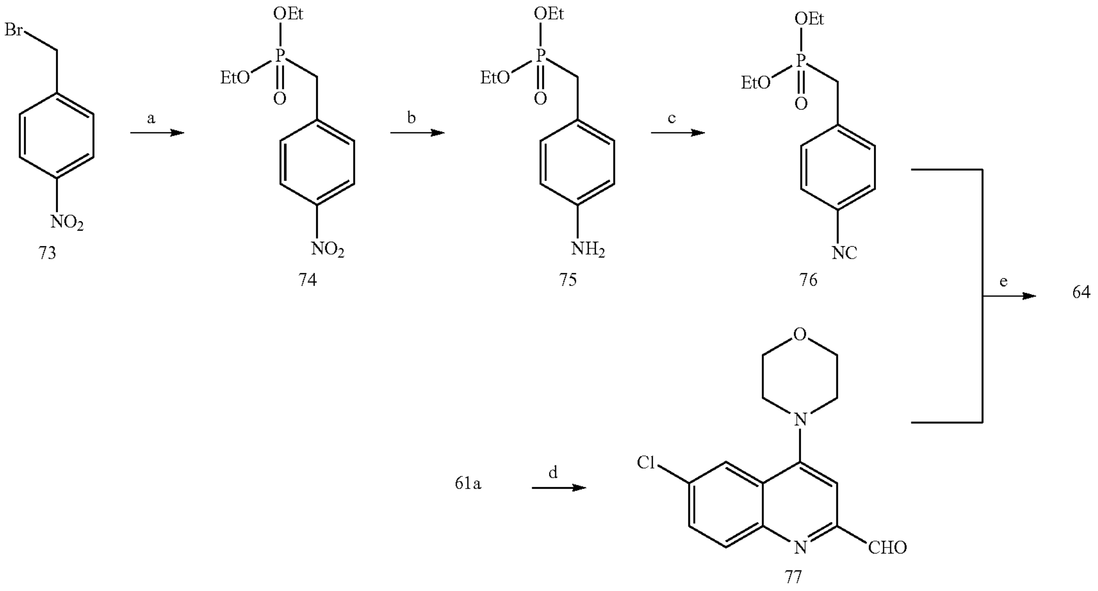

[α]Reagents and conditions: a) triethylphosphite, reflux, 20 h, 88%; b) Pd/C, H$_2$, MeOH, overnight, 75%; c) 50% NaOH, CHCl$_3$, tetrabutylammonium bromide, DCM, r.t. to 40° C., 2 h, 80%; d) SeO$_2$, 1,4-dioxane, 80° C., 6 h, 32%; e) potassium tert-butoxide, dry DMF, r.t., 1 h, 58%.

Diversification of the amino group was achieved by nucleophilic substitutions. For examples, aminoquinoline 80a-c were prepared by mixing chloroquinoline 4c with the aminoalcohol followed by mesylation and substitution. With aminoquinolines 80a-c in hand, 2-arylvinylquinolines 81-87 were obtained by reacting with appropriate aldehydes (Scheme 6).

Scheme 6 is an example according to various embodiments illustrating Synthesis of 4-aminoarylvinylquinolines 81-87$^{\alpha}$.

Scheme 6

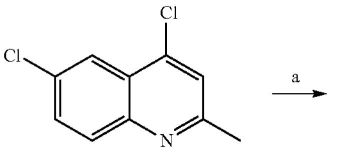

4c

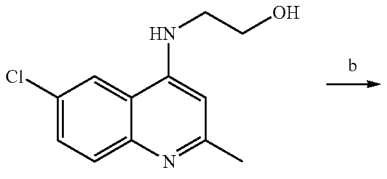

78

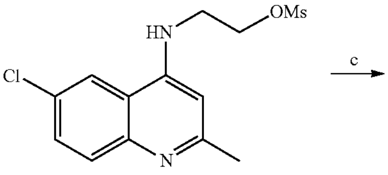

79

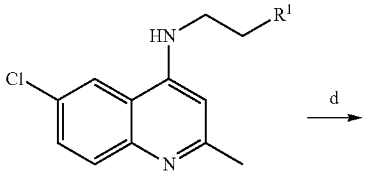

80a: $R^1$ =

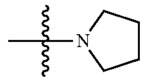

80b: $R^1$ =

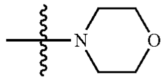

80c: $R^1$ =

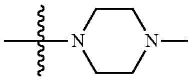

-continued

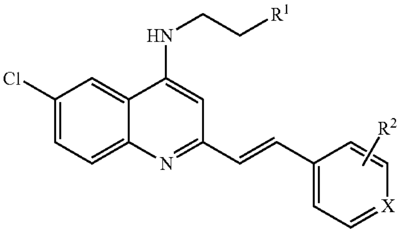

81-87
X = C or N
$R^2$ = 4-F or H $^{a}$Reagents and conditions: a) amino alcohol, EtOH, 130° C., 48 h, 97%; b) MsCl, $Et_3N$, THF, 0° C., 1 h, 72 %; c) $K_2CO_3$, amines, anhydrous $CH_3CN$, reflux, overnight, 80-94%; d) aldehydes 7a, 7h or 38c, p-$TsNH_2$, xylene, 130° C., 12 h, 79-91%.

The designed compounds 90-96 containing propylamine and butylamine moieties were synthesized in two steps (Scheme 7). First, treatment of quinoline 4c with appropriate amines 88a-c furnished aminoquinolines 89a-c, and second, aminoquinolines 89a-c were converted to 90-96 by the corresponding olefination reaction.

Scheme 7 is an example according to various embodiments illustrating the synthesis of 4-aminoarylvinylquinolines 90-96$^{\alpha}$.

Scheme 7

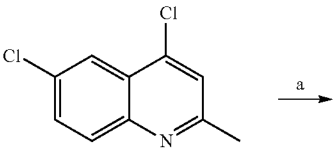

4c

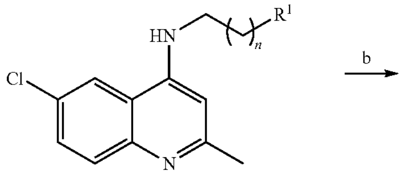

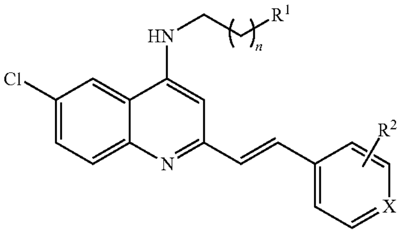

90-96
X = C and N
R2 = 4-F, H and 4-$CF_3$

-continued

89a: n = 2 $R^1$ = 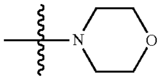

89b: n = 3 $R^1$ = 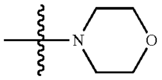

89c: n = 3 $R^1$ = 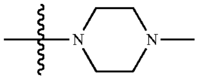

[a]Reagents and conditions: a) aliphatic amines 88a-c, 130° C., 24 h, 86-93%; b) aldehydes 7a, 7h, 7j or 38c, p-$TsNH_2$, xylene, 130° C., 12 h, 67-88%.

In Vitro Antiplasmodial Activity and Cytotoxicity

The SAR studies were focused on improving the in vitro activity of 2-arylvinylquinolines against the CQ-resistant Pf Dd2 strain. Having identified the optimal substituent at the C6 position and aromatic motif (phenyl and pyridyl) at the C2 position of quinoline scaffold, focus was placed on exploring various types of nitrogen-containing groups at C4 position. As a result, the first subset of analogues 62-72 were prepared by incorporating morpholine, pyrrolidine, 1-(2-pyridyl)piperazine, 4-piperidinoaniline and bipiperidine directly to the arylvinylquinoline scaffold, and they were screened for antimalarial activity (Table 4). These compounds generally showed moderate to low activity against Dd2 strain, with $EC_{50}$ values ranging from 428.0±15.0 to 6753.3±1076.0 nM. Unexpectedly, isonitrile compound 64 did not show significant increase in the antimalarial activity ($EC_{50}$>1000 nM). Meanwhile, it was discovered that styrylquinoline (R=4-NC) containing N,N-dimethylaminoethylamino group was less potent than compound 29 (data not shown). Compound 72 bearing a 2-picolylmethylamine moiety, the most active one in this subset, had an $EC_{50}$ value of 155.5±34.5 nM.

Inspired by the results of dimethylaminoethylamine side-chain, the second subset of analogues 81-96 were synthesized by attaching different alkylamines. These analogues displayed promising activity with $EC_{50}$ values below 100 nM, and the majority of them were more potent than the positive control compound according to Formula 1. The nitrogen atom spacing was also screened in this subset of analogues. For the morpholinylalkylamine series, arylvinylquinolines with tetramethylene linker showed much better activity than that with di- or trimethylene linker as demonstrated by the most potent compounds 92 ($EC_{50}$=2.4±1.1 nM) and 93 ($EC_{50}$=9.9±1.3 nM), displaying almost 2-fold, 3-fold and 13-fold improved potency as compared to the counterparts 81, 90 and 84, respectively. However, this linker length preference was inconclusive for N-methylpiperazinylalkylamine series. For example, compound 96 containing a 4-carbon linker was slightly more active compared to the corresponding analogue 87, whereas compound 86 bearing a 2-carbon linker was nearly 2.5 times more potent than analogue 95.

Table 4 shows antimalarial activity of targets, according to Formula 7, against CQ-resistant (Dd2) strain. The targets had structures according to Formula 7, with moieties as shown in Table 4.

Formula 7

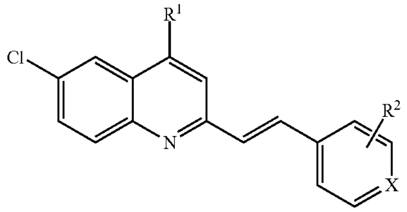

TABLE 4

| Compd. | $R^1$ | X | $R^2$ | $EC_{50}$ (nmol) |
|---|---|---|---|---|
| 62 | 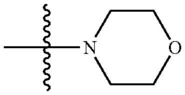 [SMILES: *N1CCOCC1] | C | 4-F | 6753.3 ± 1076.0 |
| 63 | 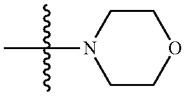 | N | H | 3590.0 ± 870.0 |
| 64 | 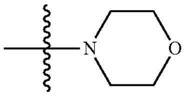 | C | 4-NC | 1007.6 ± 84.2 |
| 65 | 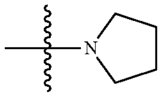 | C | 4-F | 428.0 ± 15.0 |
| 66 | 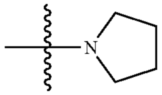 [SMILES: *N1CCCC1] | N | H | 1185.0 ± 175.0 |
| 67 | 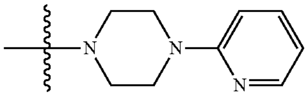 [SMILES: *N1CCN(c2ccccn2)CC1] | C | 4-F | 3300.0 ± 60.0 |
| 68 | 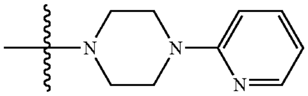 [SMILES: *N1CCN(c2ccccn2)CC1] | N | H | 2570.0 ± 610.0 |
| 69 | 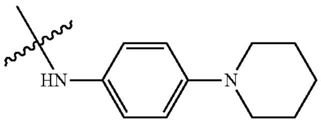 [SMILES: *Nc1ccc(N2CCCCC2)cc1] | C | 4-F | 666.7 ± 116.7 |
| 70 | 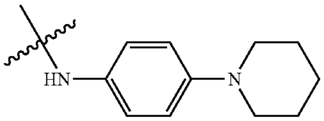 [SMILES: *Nc1ccc(N2CCCCC2)cc1] | N | H | 793.3 ± 81.3 |
| 71 | 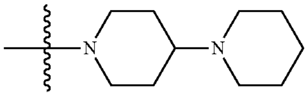 [SMILES: *N1CCC(N2CCCCC2)CC1] | C | 4-F | 486.7 ± 69.5 |

TABLE 4-continued

| Compd. | $R^1$ | X | $R^2$ | $EC_{50}$ (nmol) |
|---|---|---|---|---|
| 72 | 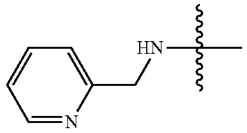 [SMILES: *NCc1ccccn1] | C | 4-F | 155.5 ± 34.5 |
| 81 | 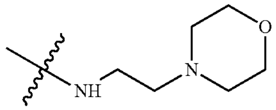 [SMILES: *NCCN1CCOCC1] | C | 4-F | 24.2 ± 0.8 |
| 82 | 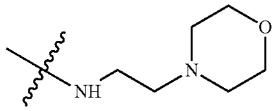 | N | H | 136.9 ± 14.6 |
| 83 | 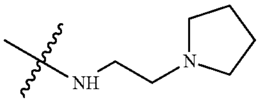 [SMILES: *NCCN1CCCC1] | C | 4-F | 92.3 ± 5.8 |
| 84 | 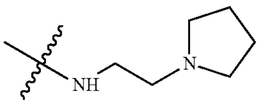 [SMILES: *NCCN1CCCC1] | C | H | 106.9 ± 8.4 |
| 85 | 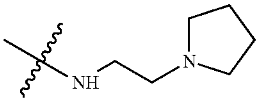 [SMILES: *NCCN1CCCC1] | N | H | 67.7 ± 11.6 |
| 86 | 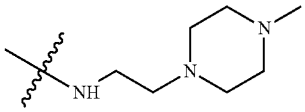 [SMILES: *NCCN1CCN(C)CC1] | C | 4-F | 15.3 ± 3.4 |
| 87 | 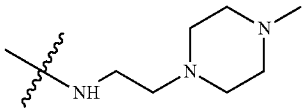 [SMILES: *NCCN1CCN(C)CC1] | N | H | 53.3 ± 8.5 |
| 90 | 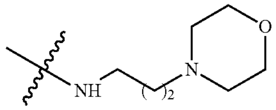 | C | 4-F | 40.8 ± 5.6 |
| 91 | 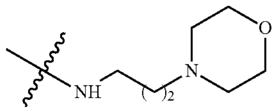 | C | 4-$CF_3$ | 84.8 ± 6.3 |
| 92 | 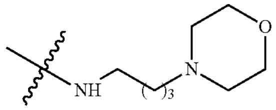 | C | 4-F | 2.4 ± 1.1 |
| 93 | 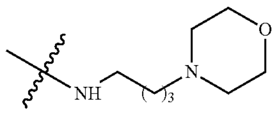 | N | H | 9.9 ± 1.3 |

TABLE 4-continued

| Compd. | $R^1$ | X | $R^2$ | $EC_{50}$ (nmol) |
|---|---|---|---|---|
| 94 | 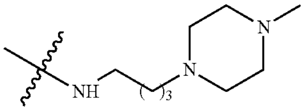 | C | H | 58.9 ± 8.8 |
| 95 | 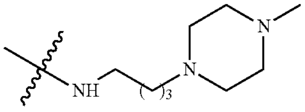 | C | 4-F | 43.0 ± 7.5 |
| 96 | 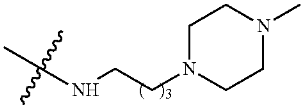 | N | H | 33.4 ± 5.4 |

Example 5

A purpose of this example was to demonstrate synthesis and testing of analogues containing various fluorinated substituents and conjugated double bonds. The synthesis of arylvinylquinolines 98-114 were commenced from methylquinoline 89b and appropriate aldehydes 7i or 97a-p (Scheme 8 and Tables 6A and 6B) using the identical procedures described for compounds 90-96.

Scheme 8 is an example according to various embodiments illustrating the synthesis of 4-morpholinobutylaminoarylvinylquinolines 98-114[α].

Scheme 8

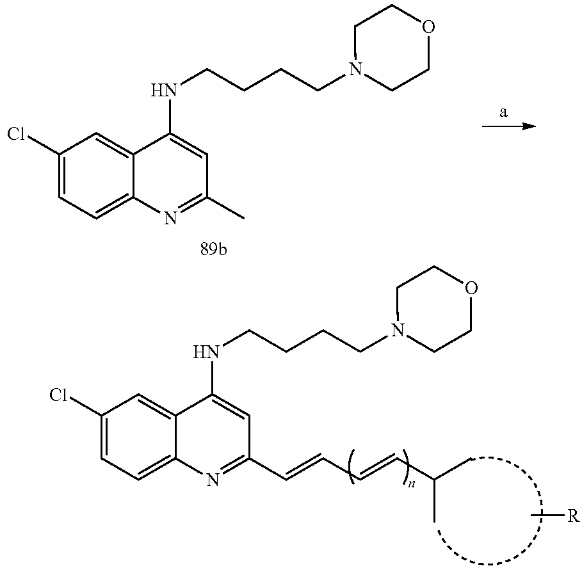

89b 98-114
n = 0 or 1

[α]Reagents and conditions: a) aldehydes 7i and 97a-p, p-TsNH2, xylene, 130° C., 12 h, 52-92%.

To evaluate the importance of the vinyl group, arylquinolines 119 and 120 were synthesized from 4-chloroaniline 1c (Scheme 9 and Tables 6A and 6B). Briefly, aniline 1c and ethyl benzoylacetate 115 or ethyl isonicotinoyl acetate 116 were condensed in the presence of PPA to give hydroxyquinolines 117a and 117b, respectively, which were transformed into arylquinolines 118a and 118b. Subsequent nucleophilic substitution with 4-morpholinobutanamine furnished 4-aminoarylvinylquinolines 119 and 120, respectively.

Scheme 9 is an example according to various embodiments illustrating the synthesis of 4-morpholinobutylaminoarylquinolines 119-120[α].

Scheme 9

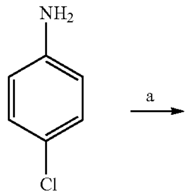

1c

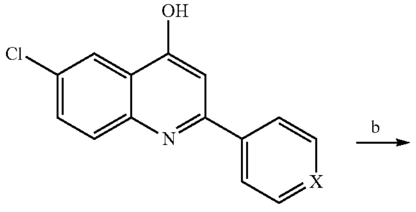

117a X = C
117b X = N

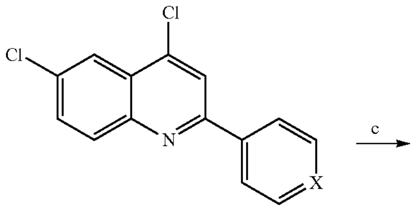

118a-b

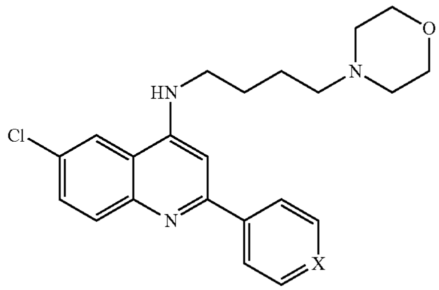

119 X = C
120 X = N

[α]Reagents and conditions: a) ethyl benzoylacetate 115 or ethyl isonicotinoyl acetate 116, 150° C., PPA, 6 h; b) phosphorus oxychloride, 105° C., 2 h, 20-45% for two steps; c) 4-morpholinobutanamine, 130° C., 24 h, 43-49% yield.

In Vitro Antiplasmodial Activity and Cytotoxicity

The SAR studies were focused on improving the in vitro activity of 2-arylvinylquinolines against the CQ-resistant Pf Dd2 strain. After C4-substitution optimization, it was determined that arylvinylquinolines containing 4-morpholinebutanamine motif (92 and 93) were good benchmark molecules for further medicinal chemistry study. In this series for C2-substituents screening, the investigation was focused on of fluorine-containing aromatics. Given the wide use of fluorine substitution in drug discovery to improve biological activity, permeability and to address pharmacokinetic issues and in light of morpholine as a privileged structure with advantageous physicochemical, biological, and metabolic properties, it was expected to produce some synergistic biological effects when these two privileged motifs were combined into one molecule. For this reason, arylvinylquinolines 98-114 were prepared with the optimal 4-morpholinebutanamine at C4 position to evaluate their capability to suppress the growth of Dd2 strain. The results are summarized in Table 5. Compound 100 with a 3-trifluoromethyl group showed comparable activity to its para positional isomer 98, which was 3-fold more potent than the ortho positional isomer 99 ($EC_{50}$=103.6±7.2 nM). This result provided additional evidence that ortho-substituents at the phenyl ring might compromise the antimalarial potency. Replacement of 4-trifluoromethyl group with 4-trifluoromethoxy substituent afforded compound 101, resulting in slightly decreased activity. A noteworthy observation was that introduction of di-substituted fluorinated phenyl ring caused significant loss of antimalarial potency as observed in analogues 102-105. It was also observed that compounds 105 and 104 were nearly 7 times and 2.5 times more active than 103, respectively, confirming that fluorine substituent at the para position of phenyl ring was favorable to improve the antimalarial activity. Further fluorination on the phenyl ring dramatically lowered the activity, rendering compounds 106-108 less active than the benchmark molecule 92. Collectively, the SAR demonstrated that monofluorination at para-position is best choice within current scope of screening and any positional deviation or excessive fluorination is disadvantageous for the antimalarial potency. Additionally, these results suggested that there is limited space available for the target(s) interaction, with ortho-position and steric effects being particularly sensitive to substitution on the styryl scaffold.

Unexpectedly, introduction of fluorine atom at the pyridine ring did not cause the increased antimalarial activity but diminished the potency. For instance, compound 109 with 3-fluoro substituent ($EC_{50}$=79.6±11.8 nM) was almost 7.5-fold less active than the counterpart 93 (Table 4, $EC_{50}$=9.9±1.3 nM). Interestingly, both pyridylethenylquinolines 109 and 111 demonstrated much weaker inhibitory activity than compound 110 ($IC_{50}$=54.6±16.5 nM). Additionally, among this series, compound 112 with 3-fluoropyridine moiety displayed the weakest inhibitory effect on Dd2 strain with $EC_{50}$ values of 197.1±16.5 nM. Again, these results implied that the ortho substitution at the aromatic ring could intervene the target interactions that were quite sensitive to the steric effect and the orientation of the aromatic ring.

Analogues with different number of double bonds (113-114 and 119-120) were also assessed for their in vitro antimalarial activity. Compound 113 and 114 with two double bonds exhibited much lower activity than the benchmark compounds, implying one double bond is a better choice for the antimalarial potency. Additional supports for the crucial role of vinyl group came from the evaluation of analogues without any double bond. As shown in Table 5, the great loss of activity was observed in arylquinolines 119 and 120 ($EC_{50}$>400 nM). Thus, it was concluded that one double bond between the quinoline core and the aromatic ring is required for the antiplasmodial activity, highlighting the uniqueness of the chemical scaffold according to various embodiments. Meanwhile, these results well supported the initial hypothesis that the arylvinyl moiety plays a crucial role in the target(s) interaction.

Table 5 shows antimalarial activity of targets, according to Formula 8, against CQ-resistant (Dd2) strain. The targets had structures according to Formula 8, with moieties as shown in Table 5.
Formula 8
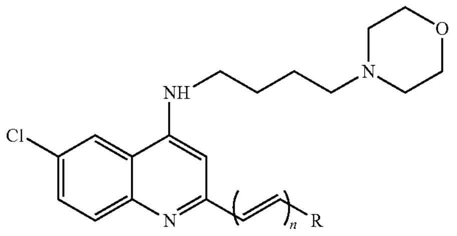
TABLE 5
| Compd. | n | R | $EC_{50}$ (nmol) |
|---|---|---|---|
| 98 | 1 | 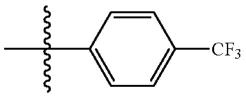 [SMILES: *c1ccc(C(F)(F)F)cc1] | 30.7 ± 5.2 |
| 99 | 1 | 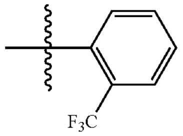 [SMILES: *c1ccccc1C(F)(F)F] | 103.6 ± 7.2 |
| 100 | 1 | 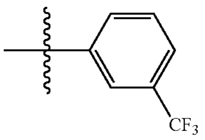 [SMILES: *c1cccc(C(F)(F)F)c1] | 33.9 ± 1.4 |
| 101 | 1 | 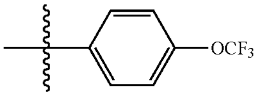 [SMILES: *c1ccc(OC(F)(F)F)cc1] | 56.6 ± 7.6 |
| 102 | 1 | 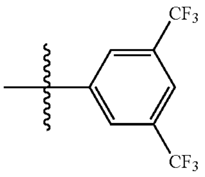 | 108.0 ± 8.0 |
| 103 | 1 | 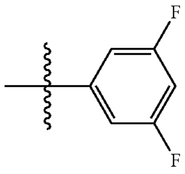 [SMILES: *c1cc(F)cc(F)c1] | 185.3 ± 34.1 |
| 104 | 1 | 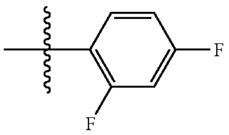 [SMILES: *c1ccc(F)cc1F] | 72.6 ± 17.2 |
TABLE 5-continued
| Compd. | n | R | $EC_{50}$ (nmol) |
|---|---|---|---|
| 105 | 1 | 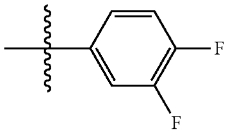 [SMILES: *c1ccc(F)c(F)c1] | 25.5 ± 6.1 |
| 106 | 1 | 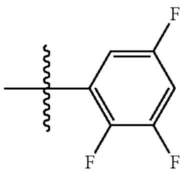 [SMILES: *c1cc(F)cc(F)c1F] | 587.5 ± 255.5 |
| 107 | 1 | 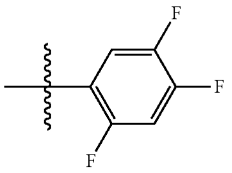 [SMILES: *c1cc(F)c(F)cc1F] | 196.7 ± 39.7 |
| 108 | 1 | 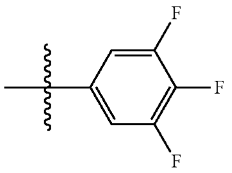 [SMILES: *c1cc(F)c(F)c(F)c1] | 130.1 ± 34.9 |
| 109 | 1 | 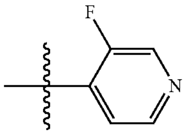 [SMILES: *c1ccncc1F] | 79.6 ± 11.8 |
| 110 | 1 | 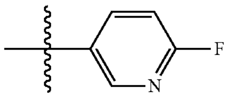 [SMILES: *c1ccc(F)nc1] | 54.6 ± 16.5 |
| 111 | 1 | 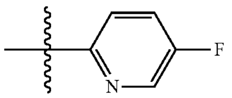 | 73.1 ± 11.9 |
| 112 | 1 | 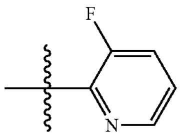 [SMILES: *c1ncccc1F] | 197.1 ± 81.2 |
| 113 | 2 | 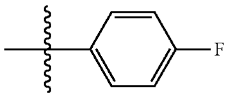 [SMILES: *c1ccc(F)cc1] | 96.5 ± 24.4 |
| 114 | 2 | 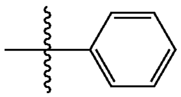 [SMILES: *c1ccccc1] | 142.7 ± 18.6 |
| 119 | 0 | 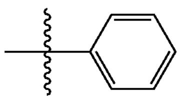 [SMILES: *c1ccccc1] | 422.7 ± 62.7 |

TABLE 5-continued

| Compd. | n | R | $EC_{50}$ (nmol) |
|---|---|---|---|
| 120 | 0 | 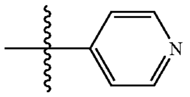 [SMILES: *c1ccncc1] | 796.3 ± 161.3 |

Example 6

A purpose of this example was to demonstrate analysis of twelve arylvinylquinolines that were selected for further antiplasmodium activity and cytotoxicity assay. As shown in Tables 6A and 6B, the SAR trends observed toward the 3D7 strain were similar to that observed toward the Dd2 strain. For instance, compound 30 with 2-fluorine group ($EC_{50}$=55.9±9.5 nM) showed remarkably diminished potency as compared with the corresponding 4-fluorine (compound 29, $EC_{50}$=8.7±0.5 nM) or 3-fluorine analogues (compound 31, $EC_{50}$=23.0±2.8 nM). It was worth noting that all selected arylvinylquinolines were more active against Dd2 strain than against 3D7 strain (RI<1), except for compound 86 (RI=1), suggesting no cross-resistance induced by arylvinylquinolines between CQ-resistant and CQ-sensitive parasites. By contrast, RI of CQ is almost 10.

The cytotoxicity trend appeared to be coincident with their antiplasmodial activity, e.g. compounds 24 vs 29, 72 vs 81 vs 86, 93 vs 96 and 98 vs 105. Nevertheless, it was observed that the position of fluorine atom at the phenyl ring has marginal effect on their cytotoxic activities, as seen with compounds 29-31. Compound 92 containing tetramethylene linker showed nearly 10-fold and 4.8-fold improvement in inhibitory activity against 3D7 strain and cytotoxicity relative to compound 81, respectively. Notably, all compounds tested showed good selectivity profiles (SI>120), especially for compounds 24, 29 and 92 (SI>1000), indicating good safety windows.

Tables 6A and 6B show antiplasmodium activity and cytotoxicity of synthesized analogues. The targets had structures according to Formula 2, with moieties as shown in Tables 6A and 6B, wherein n=1. As shown in Tables 6A and 6B, multiple $R_2$ groups may be present.

Formula 2

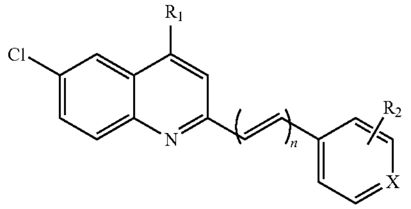

TABLE 6A

| | | | | Antiplasmodium activity | | |
|---|---|---|---|---|---|---|
| Compd. | $R_1$ | X | $R_2$ | Dd2 | 3D7 | RI[a] |
| 24 | 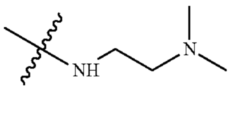 [SMILES: *NCCN(C)C] | C | 4-$CF_3$ | 10.9 ± 1.9 | 16.8 ± 0.8 | 0.6 |
| 29 | | C | 4-F | 4.8 ± 2.0 | 8.7 ± 0.5 | 0.6 |
| 30 | | C | 2-F | 26.0 ± 0.9 | 55.9 ± 9.5 | 0.5 |
| 31 | | C | 3-F | 5.9 ± 1.4 | 23.0 ± 2.8 | 0.3 |
| 50 | | N | H | 28.8 ± 5.0 | 56.6 ± 11.2 | 0.5 |
| 72 | 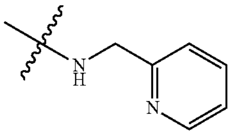 [SMILES: *NCc1ccccn1] | C | 4-F | 155.5 ± 34.5 | 248.3 ± 35.1 | 0.6 |
| 81 | 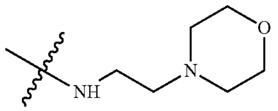 [SMILES: *NCCN1CCOCC1] | C | 4-F | 24.2 ± 0.8 | 41.8 ± 12.7 | 0.6 |
| 86 | 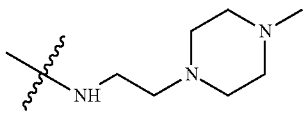 [SMILES: *NCCN1CCN(C)CC1] | C | 4-F | 15.3 ± 3.4 | 15.7 ± 2.9 | 1.0 |
| 92 | 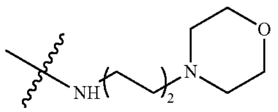 | C | 4-F | 2.4 ± 1.1 | 6.9 ± 1.3 | 0.3 |
| 93 | | N | H | 9.9 ± 1.3 | 20.8 ± 4.4 | 0.5 |
| 96 | 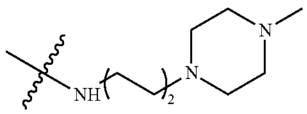 | N | H | 33.4 ± 5.4 | 36.1 ± 11.3 | 0.9 |

TABLE 6A-continued
| | | | | Antiplasmodium activity | | |
|---|---|---|---|---|---|---|
| Compd. | $R_1$ | X | $R_2$ | Dd2 | 3D7 | RI[a] |
| 98 | 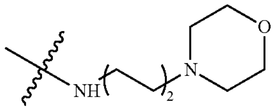 | C | 4-$CF_3$ | 30.7 ± 5.2 | 73.8 ± 9.7 | 0.4 |
| 105 | | | 3,4-diF | 25.5 ± 6.1 | 27.6 ± 1.2 | 0.9 |
| Compd. of Formula 1 | — | | | 67.0 ± 8.0 | 119.0 ± 3.0 | 0.6 |
| Chloroquine | — | | | 174.0 ± 15.5 | 17.8 ± 5.5 | 9.8 |
[a]RI is resistance index = [$IC_{50}$ (Dd2)/$IC_{50}$ (3D7)].
TABLE 6B
| | | | | Cytotoxic activity | |
|---|---|---|---|---|---|
| Compd. | $R_1$ | X | $R_2$ | HepG2 | SI[b] |
| 24 | 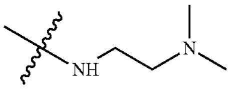 | C | 4-$CF_3$ | 11235 ± 1855 | 1031 |
| 29 | | C | 4-F | 5331.6 ± 964.9 | 1110 |
| 30 | | C | 2-F | 4827.3 ± 1072 | 186 |
| 31 | | C | 3-F | 4777.4 ± 1588 | 810 |
| 50 | | N | H | 6110.6 ± 1046 | 212 |
| 72 | 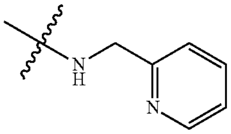 [SMILES: *NCc1ccccn1] | C | 4-F | 19760.6 ± 3272 | 127 |
| 81 | 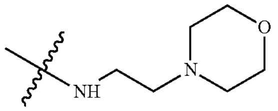 | C | 4-F | 17204.6 ± 3299 | 711 |
| 86 | 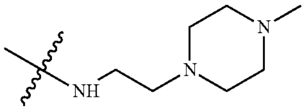 [SMILES: *NCCN1CCN(C)CC1] | C | 4-F | 3195.2 ± 490.8 | 209 |
| 92 | 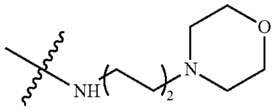 | C | 4-F | 3547.0 ± 384.1 | 1478 |
| 93 | | N | H | 5670.1 ± 1162 | 561 |
| 96 | 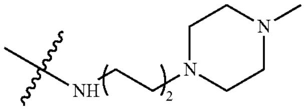 | N | H | 8377.7 ± 2576 | 251 |
| 98 | 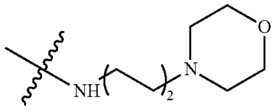 | C | 4-$CF_3$ | 10178.2 ± 2391 | 332 |
| 105 | | | 3,4-diF | 6135.2 ± 1222 | 241 |
| Compd. of Formula 1 | — | | | 12920.0 ± 70.1 | 192 |
| Chloroquine | — | | | 10430.0 ± 860.0 | 60 |
[b]SI is selectivity index = [$IC_{50}$ (HepG2)/$IC_{50}$ (Dd2)].

Example 7

A purpose of this example was to demonstrate Metabolic Stability and Preliminary Metabolite Identification. To assess the metabolic stability, the selected compounds were subjected to an in vitro microsomal turnover assay with mouse liver microsomal preparations. This assay determines the percentage of the parent compound residues after 60 min incubation (Table 7). It appeared that compounds bearing 4-trifluoromethyl group at the phenyl ring exhibited better metabolic stability than that with 4-fluoro group, as demonstrated by compounds 24 ($t_{1/2}$=104.2 min) vs 29 ($t_{1/2}$=55.2 min) and 92 ($t_{1/2}$=22.2 min) vs 98 ($t_{1/2}$=64.9 min). The intrinsic stability of N, N-dimethylaminoethylamine moiety was superior to 2-pyridinemethanamine or 2-(4-methylpiperaziyl) ethanamine groups, e.g. compounds 29 vs 72 ($t_{1/2}$=65.3 min) and 86 ($t_{1/2}$=60.3 min). Morpholine motif appeared to be the most labile group upon enzymatic degradation, which was not in line with the previous study of CQ derivatives. The typical example was that compound 92 had the shortest half-life time ($t_{1/2}$=22.2 min) in this series. Another observation was that replacing the phenyl ring with pyridine in arylvinylquinoline rendered them more susceptible to hepatic metabolism, such as the case of compound 50 and compound 93 ($t_{1/2}$=14.4 min), suggesting that pyridyl ring had no advantages over benzenoids in the microsomal stability. The present experiments indicated that C4 amino side-chain and arylvinyl group significantly affected their metabolic stability.

In the context of the present study, the tentative metabolites were identified by LC-MS after 15, 30, 60 min incubations. N-dealkylation from the tertiary terminal amine and oxidation of arylvinylquinoline scaffold seemed to be the major pathways for the metabolic decomposition, which was consistent with the previous studies on 4-aminoquinolines metabolism, and P450 mediated oxidation in liver microsomes. For example, the microsomal metabolites of a compound according to Formula 1 were mainly derived from N-deethylation of the tertiary amine (monodesethyl a compound according to Formula 1, a compound according to Formula 1-M1), O-demethylation (a compound according to Formula 1-M2), oxidation of styrylquinoline (a compound according to Formula 1-M3) and the reduction of nitro group (three minor metabolites). The tentatively assigned metabolites of compound 29 included monodemethylated (29-M1), bidesmethylated (29-M2) and oxidized products (29-M3). The same decomposition pathway was not observed for compound 24, albeit with the identical C4 side-chain, which could explain the different metabolic stability profiles of 24, 29 and a compound according to Formula 1. Although N-demethylation was the primary metabolic route for compound 24, its half-life time was acceptable compared to other literature reports.

The metabolic instability of arylvinylquinolines 92, 93, 98 and 105 was largely attributed to the breakage of the morpholine ring (alkanolamine metabolite M1 and primary amine metabolite M2). Among this series, compound 93 was the most susceptible to hepatic metabolism, and oxidative metabolites 93-M3 and 93-M4 were observed in addition to ring-opening metabolites M1 and M2.

Table 7 shows in vitro metabolism in mouse liver microsomes.

TABLE 7

| Compd. | % remaining after 60 min | Projected $t_{1/2}$ (min) | Clint (μL/min/mg) |
|---|---|---|---|
| 24 | 67.1 | 104.2 | 13.3 |
| 29 | 47.1 | 55.2 | 25.1 |
| 31 | 38.2 | 43.2 | 32.1 |
| 50 | 15.5 | 22.3 | 62.2 |
| 72 | 52.9 | 65.3 | 21.2 |
| 86 | 50.2 | 60.3 | 23.0 |
| 92 | 15.4 | 22.2 | 62.4 |
| 93 | 5.62 | 14.4 | 96.2 |
| 98 | 52.7 | 64.9 | 21.4 |
| 105 | 19.9 | 25.8 | 53.7 |
| a compound according to Formula 1 | 36.7<br>47.8[a] | 41.5<br>56.2[a] | 33.4<br>— |

[a]Values reported from an initial study.[35]

Example 8

A purpose of this example was to demonstrate that arylvinylquinolines, according to various embodiments, block trophozoite stage in Pf asexual life cycle. Accurate definition of the timing of action of antimalarial agents could give valuable insights into the developmental growth and clinical clearance of the parasite. To further understand the antimalarial activity of arylvinylquinolines, the developmental stage specific action of the most promising compound 24 was determined by both microscopy and flow cytometry analysis. Tightly synchronized cultures were exposed to $5\times EC_{50}$ concentration of compound 24 at 6, 18, 30 and 42 hours post-invasion (HPI) of the merozoites. Microscopic analysis of Giemsa-stained-thin smears and flow cytometric evaluation were performed at 12 h intervals.

Figure 2A:
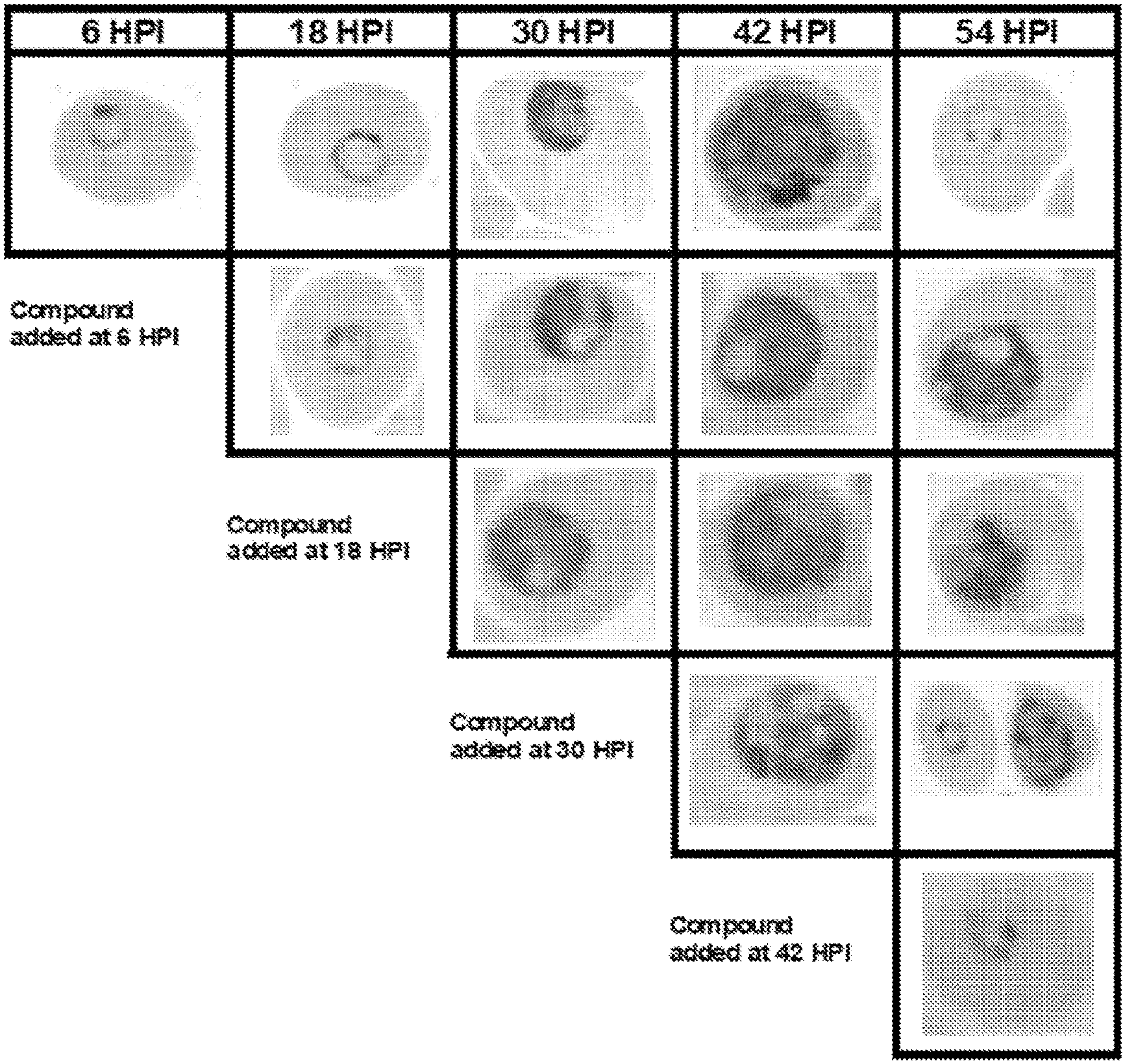
FIG. 2A: is an example according to various embodiments illustrating samples for Giemsa staining taken every 12 h showing stage-specific inhibition of *P. falciparum* growth by compound 24 from tightly synchronized Dd2 parasites treated at 6, 18, 30 and 42 h post-invasion (hpi) with compound 24 at $5\times EC_{50}$ concentration.
Figure 2B:
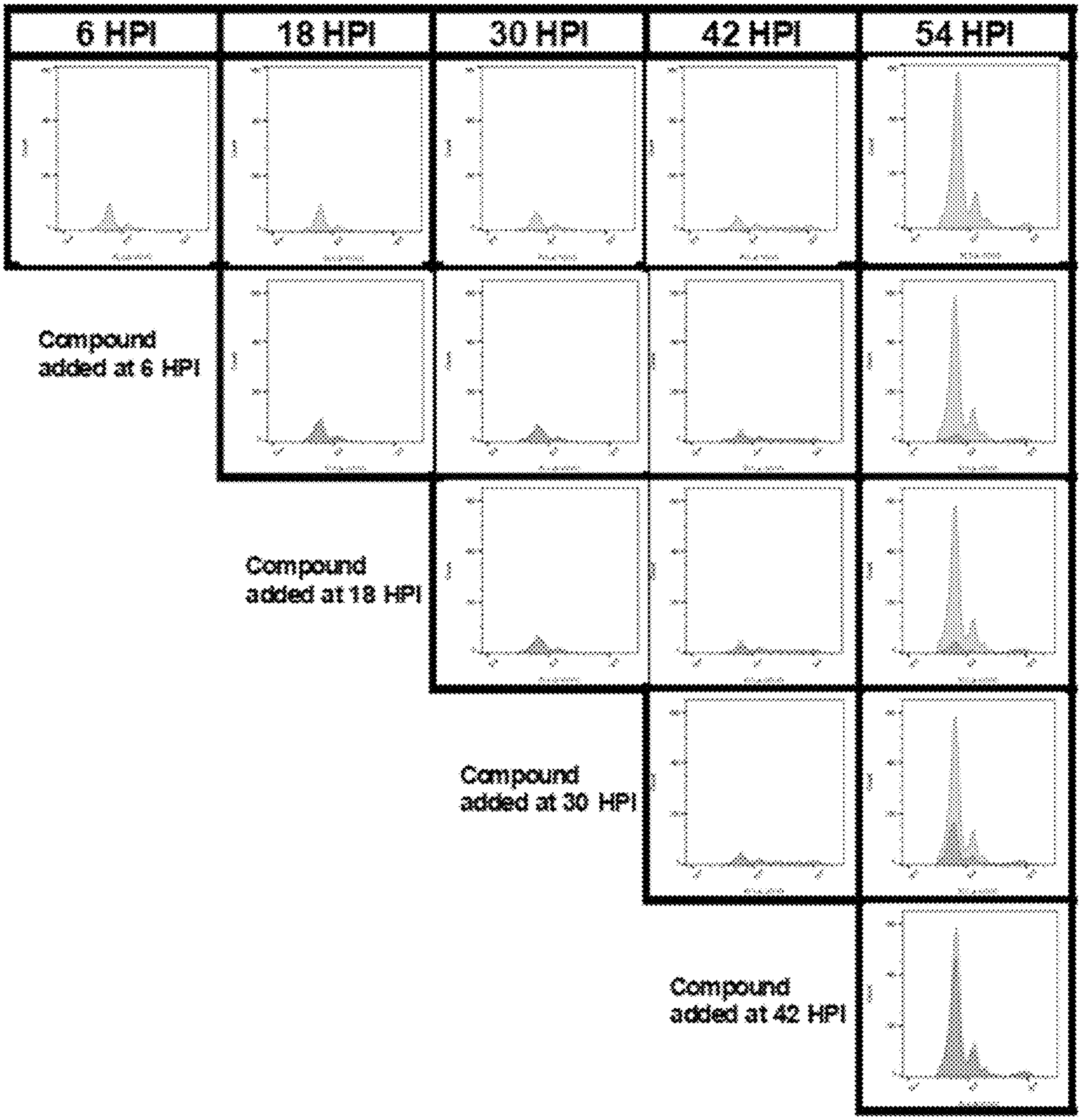
FIG. 2B: is an example according to various embodiments illustrating flow cytometry analysis taken every 12 h showing stage-specific inhibition of *P. falciparum* growth by compound 24 from tightly synchronized Dd2 parasites treated at 6, 18, 30 and 42 h post-invasion (hpi) with compound 24 at $5\times EC_{50}$ concentration.

In FIGS. 2A and 2B, the results are representative of three independent biological replicates. FIG. 2A is an example according to various embodiments illustrating samples for Giemsa staining taken every 12 h showing stage-specific inhibition of *P. falciparum* growth by compound 24 from tightly synchronized Dd2 parasites treated at 6, 18, 30 and 42 h post-invasion (hpi) with compound 24 at $5\times EC_{50}$ concentration. FIG. 2B is an example according to various embodiments illustrating flow cytometry analysis taken every 12 h showing stage-specific inhibition of *P. falciparum* growth by compound 24 from tightly synchronized Dd2 parasites treated at 6, 18, 30 and 42 h post-invasion (hpi) with compound 24 at $5\times EC_{50}$ concentration.

As seen in FIG. 2A, the untreated control cultures underwent normal cell cycle progress through trophozoite (18 HPI), early schizont (30 HPI), late schizont/segmenter (42 HPI) and reappeared ring (54 HPI) after reinvasion with the increased peak height and reappearance of individual peaks (FIG. 2A-B). In contrast to untreated cultures, the maturation of compound 24-treated cultures was blocked at the trophozoite stage (18 HPI) (FIG. 2A-B). Similarly, compounds 29 and 86 demonstrated stage-specific action at the trophozoite phase in Dd2 cultures. Thus, these results indicated that arylvinylquinolines eradiate blood stage parasites by arresting the trophozoite phase in Pf asexual life cycle.

Example 9

A purpose of this example was to demonstrate that arylvinylquinolines, according to various embodiments, are fast-acting parasitocidal agents. To study whether arylvinylquinolines exerted their antiplasmodial activity through a parasitocidal or parasitostatic mechanism, kill kinetic experiments in Dd2 strain were performed. Growing asynchronous Dd2 cultures were treated with 5×$EC_{50}$ concentrations of arylvinylquinolines 24, 29 and 86, dihydroartemisinin (DHA, 50 nM) and Atovaquone (6.6 nM) for different periods of time (6, 12, 24 and 48 h). After washing to remove the inhibitors at these time points, the growth of the cultures was continued to be assessed for 96 h.

FIGS. 3A, 3B, 3C, and 3D are examples according to various embodiments illustrating rate of killing and parasitocidal/parasitostatic activity determination of arylvinylquinolines. The killing rate was evaluated in asynchronous Dd2 parasite cultures exposed to 5×$EC_{50}$ concentration for (A) 6 h, (B) 12 h, (C) 24 h, and (D) 48 h. After each exposure, cultures were washed three times in RPMI, resuspended in culture media, and monitored for parasite growth daily for 4 days. DHA and Atovaquone (50 nM and 6.6 nM) were included as fast and slow acting controls, respectively. Parasitemia was determined by microscopy of Giemsa stained smear.

As can be seen from FIG. 3D, parasitemias decreased slightly when they were exposed to Atovaquone for 6, 12 and 24 h (FIG. 3A-C) and the viable parasites reduced significantly after 48 h treatment, which confirmed that Atovaquone is a slow-acting antimalarial. By contrast, the remarkable reduction in parasitemias was observed following all time points treatments with compounds 24, 29 and 86, which was similar to the killing kinetic profile of DHA (FIG. 3A-D). These results suggested that arylvinylquinolines are good parasitocidal agents with rapid clearance of parasites.

Example 10

Figure 4A:
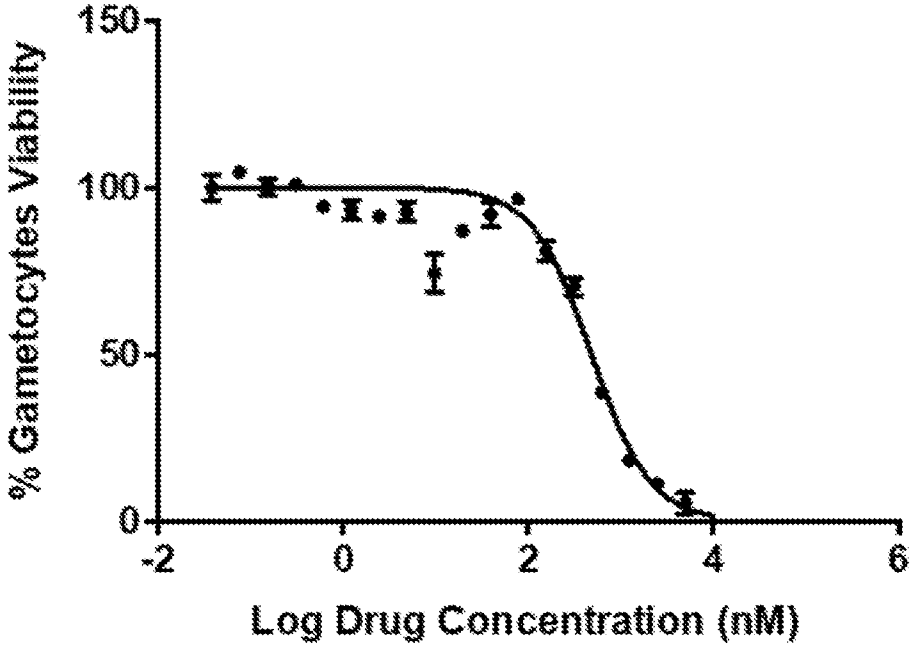
FIG. 4A: is an example according to various embodiments illustrating results showing the activity of compound 24 on gametocyte stages, based on an evaluation of the viability of gametocytes after the exposure of compound 24 on early gametocytes stages of 3D7 expressing luciferase parasite.
Figure 4B:
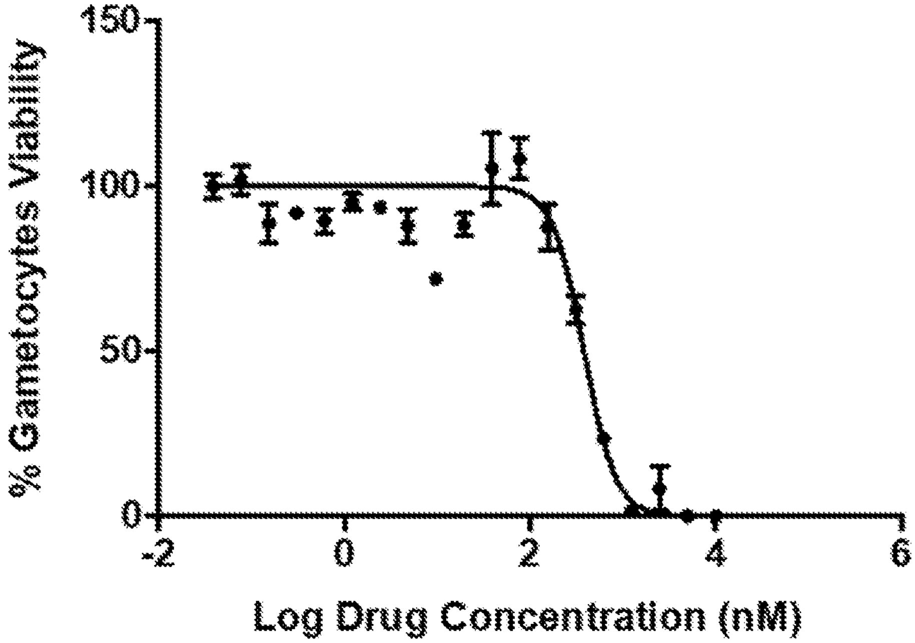
FIG. 4B: is an example according to various embodiments illustrating results showing the activity of compound 24 on gametocyte stages, based on an evaluation of the viability of gametocytes after the exposure of compound 24 on late gametocytes stages of 3D7 expressing luciferase parasite.

A purpose of this example was to demonstrate the in vitro gametocytocidal activity of arylvinylquinolines according to various embodiments. The in vitro gametocytocidal activity of arylvinylquinolines 24, 29 and 86 was evaluated, and the results are summarized in Table 8. All three compounds demonstrated the potent inhibitory activity toward early stage (I-III) gametocytes with $EC_{50}$ values in the submicromolar range. Late stage (IV-V) gametocytes are more refractory to antimalarial drugs than early-stage gametocytes and blood stage parasites, and thus fewer compounds are effective against late stage Pf gametocytes. Encouragingly, all compounds tested also displayed strong inhibitory activity toward late-stage gametocytes, among which 24 was the most active molecule with an $EC_{50}$ value of 393.6±99.4 nM (Table 8 and FIG. 4). FIGS. 4A and 4B are an examples according to various embodiments illustrating results showing the activity of compound 24 on gametocyte stages, based on an evaluation of the viability of gametocytes after the exposure of compound 24 on early (A) and late (B) gametocytes stages of 3D7 expressing luciferase parasite. In FIGS. 4A and 4B, $EC_{50}$ data represent the means and SEMs of three experiments. Therefore, arylvinylquinolines represented good leads as new antimalarials with promising dual stage (blood and gametocyte) activity. Table 8 shows the inhibition of early and late stage gametocytes.

TABLE 8

| Compd. | Early stage IC50 (nM) a | Late stage IC50 (nM) a |
|---|---|---|
| 24 | 471.5 ± 18.4 | 393.6 ± 99.4 |
| 29 | 590.7 ± 118.7 | 2049.3 ± 113.6 |
| 86 | 909.9 ± 314.2 | 2495.7 ± 423.8 |
| Methylene blue | 74.7 ± 21.9 | 107.2 ± 46.3 |
| DHA | 17.4 ± 3.7 | 37.4 ± 8.9 |

a $EC_{50}$ data represent the means and SEMs of three experiments.

Example 11

Figure 5A:
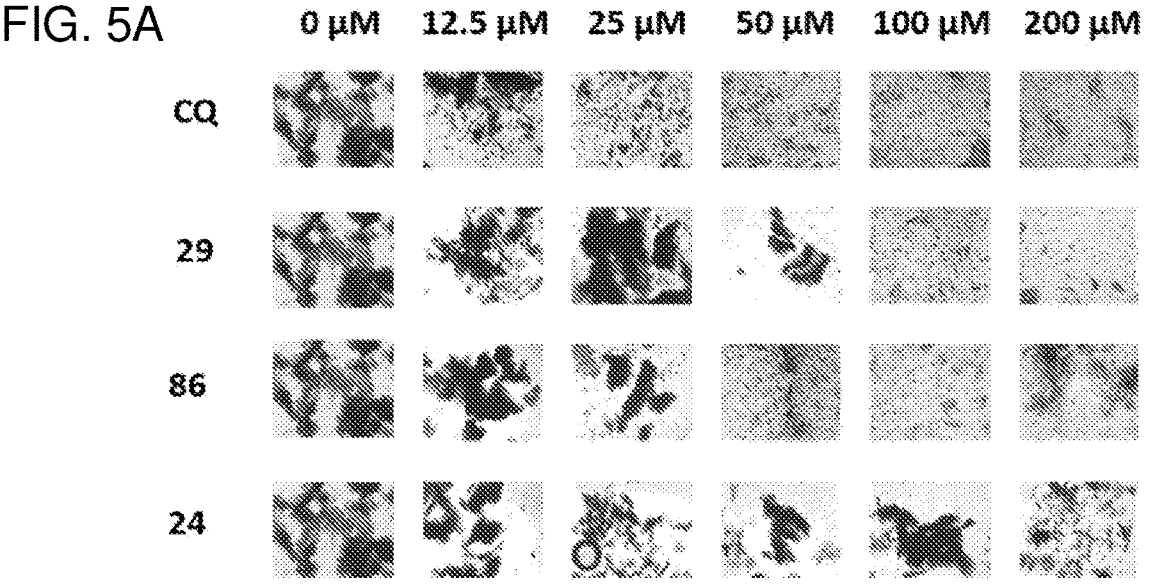
FIG. 5A: is an example according to various embodiments illustrating images of β-hematin crystals after incubation of 100 μM hemin, propionate buffer, phosphatidylcholine and, several concentrations of compound for 16 h at 37° C. Images were taken using a Nikon optical microscope, showing the effect of the 2-arylethenylaminequinoline derivatives on the β-hematin crystal formation.
Figure 5B:
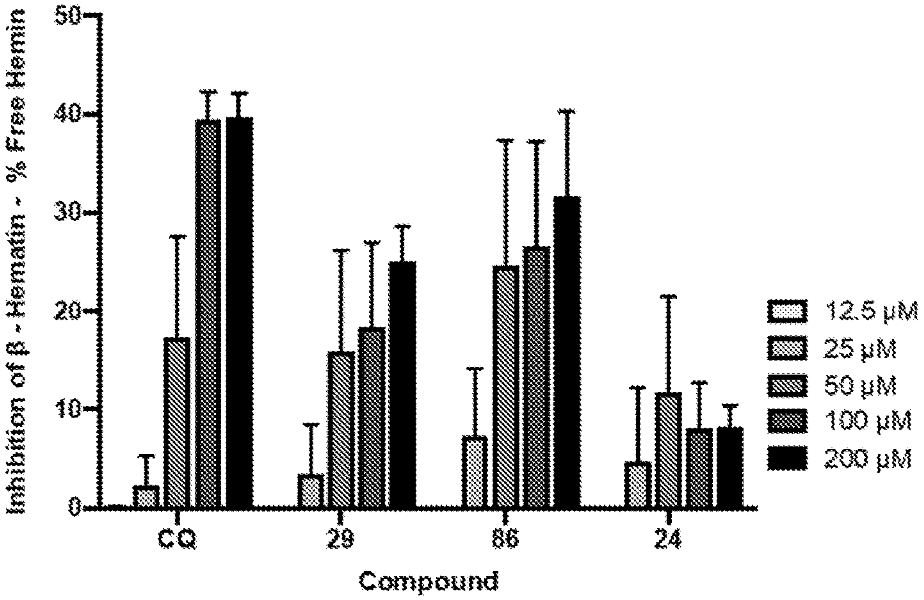
FIG. 5B: is an example according to various embodiments illustrating ree hemin, as indicative of β-hematin crystal formation, which was determined using a linear calibration curve, showing the effect of the 2-arylethenylaminequinoline derivatives on the β-hematin crystal formation.

A purpose of this example was to demonstrate the β-Hematin inhibition activity of arylvinylquinolines according to various embodiments. CQ and other aminoquinolines are known to fight against the malaria parasites by blocking hematin biocrystallization (hemozoin formation) through π-π stacking between the aminoquinoline scaffold and the heme. As a result, the accumulated toxic heme causes the parasite death by introducing oxidative membrane damage. β-hematin inhibition experiments were performed to determine possible mode of actions of arylvinylquinolines. FIG. 5A is an example according to various embodiments illustrating images of β-hematin crystals after incubation of 100 μM hemin, propionate buffer, phosphatidylcholine and, several concentrations of compound for 16 h at 37° C. Images were taken using a Nikon optical microscope, showing the effect of the 2-arylethenylaminequinoline derivatives on the β-hematin crystal formation. FIG. 5B is an example according to various embodiments illustrating ree hemin, as indicative of β-hematin crystal formation, which was determined using a linear calibration curve, showing the effect of the 2-arylethenylaminequinoline derivatives on the β-hematin crystal formation. In FIGS. 5A and 5B, the data are mean±SEM. As shown in FIG. 5A-B, CQ potently inhibited β-hematin formation, and both compounds 29 and 86 showed inhibitory activity towards β-hematin formation in a concentration-dependent manner, although their activity was much weaker than that of CQ. By comparison, compound 24 demonstrated very low activity against β-hematin crystal formation even at the highest concentration (200 μM). These results suggested that the potent antimalarial activity of arylvinylquinolines could be associated with other mechanisms, apart from inhibition of heme detoxification.

Example 12

Figure 6A:
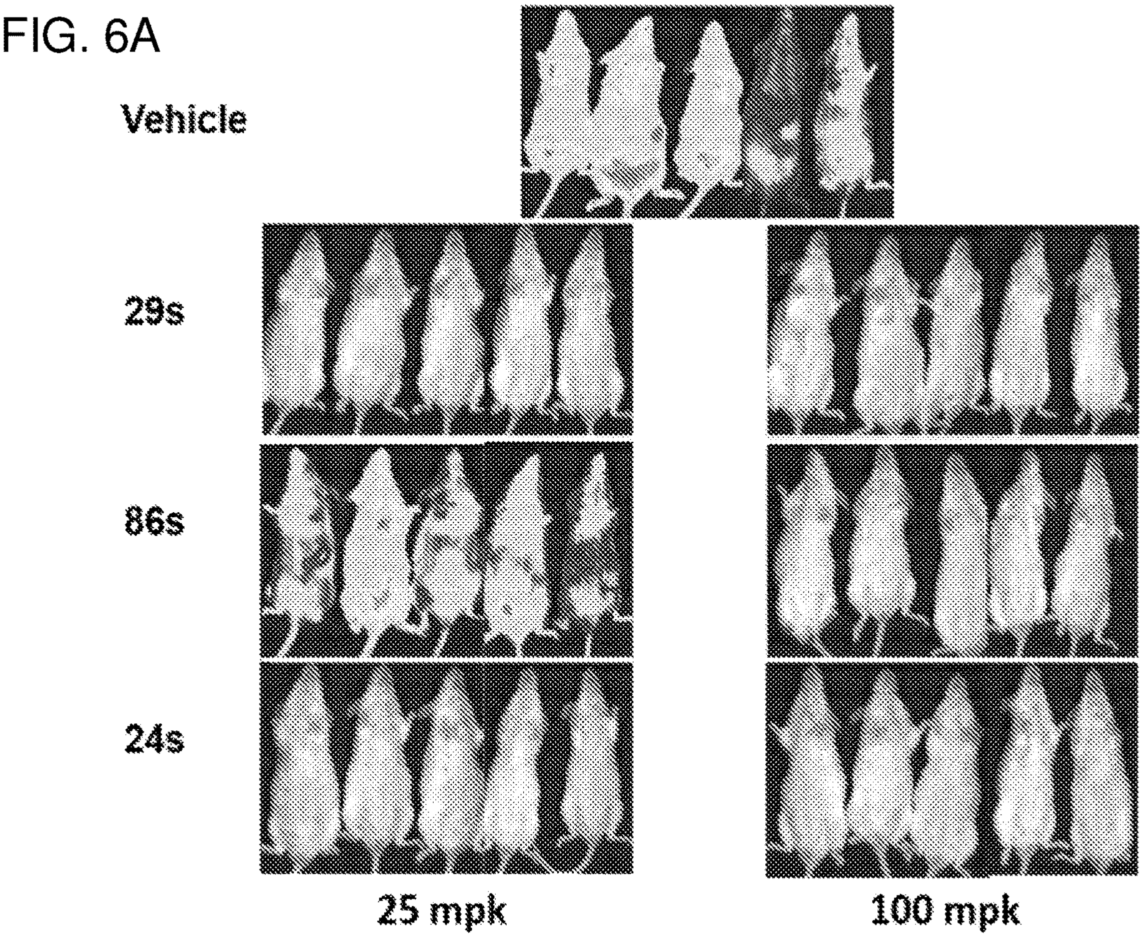
FIG. 6A: is an example according to various embodiments illustrating in vivo imaging system (IVIS) of Swiss Webster females were infected with *P. berghei* ANKA strain expressing luciferase, treated with 25 and 100 mg/kg orally once daily 48 h post-infection, demonstrating the curative properties of arylvinylquinolines derivatives according to various embodiments.
Figure 6B:
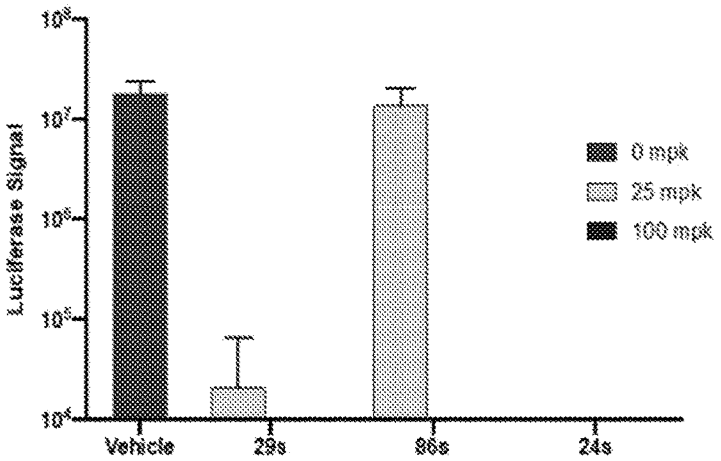
FIG. 6B: is an example according to various embodiments illustrating a chart showing the luminescence detected and quantified 7 days after infection of the Swiss Webster females shown in FIG. 6A, using an in vivo imaging system (IVIS), demonstrating the curative properties of arylvinylquinolines derivatives according to various embodiments.

A purpose of this example was to demonstrate that arylvinylquinolines, according to various embodiments, are well-tolerated and active in in vivo model. Given the robust antimalarial potency of 2-arylvinylquinolines against Dd2 and 3D7 strains and good microsomal stability profiles of 24, 29 and 86, in vivo studies were performed with these compounds on a rodent malaria model. Phosphate salts of 24, 29 and 88 were assessed (referred to hereinafter as 24 s, 29 s, and 88 s) in female Swiss Webster mice infected with *P. berghei* ANKA strain since this strain produced histopathological and immunopathological features which were particularly similar to human cerebral malaria. FIG. 6A is an example according to various embodiments illustrating in vivo imaging system (IVIS) of Swiss Webster females were infected with *P. berghei* ANKA strain expressing luciferase, treated with 25 and 100 mg/kg orally once daily 48 h post-infection. FIG. 6B is an example according to various embodiments illustrating a chart showing the luminescence detected and quantified 7 days after infection of the Swiss Webster females shown in FIG. 6A, using an in vivo imaging system (IVIS). FIGS. 6A and 6B demonstrate the curative properties of arylvinylquinolines derivatives according to various embodiments. As observed from FIG. 6A-B, all these compounds completely cured malaria infection in mice when exposed to 100 mg/kg daily by p.o. administration in a standard Peters' four-day test, and no parasites visible in any of the tested mice were observed. Although low dose (25 mg/kg) compound 88 s was ineffective for malarial infected mice, compound 29 s at this dose effectively cleared the parasites. However, marginal luminescence signal was detected in compound 29 s-treated mice, suggesting that there still could be parasites circulating. Actually, this signal can also arise from dying parasites. It was unexpectedly discovered found that 24 s provided full protection and cure at 25 mg/kg with no bioluminescence signals detected after treatment.

Figure 7:
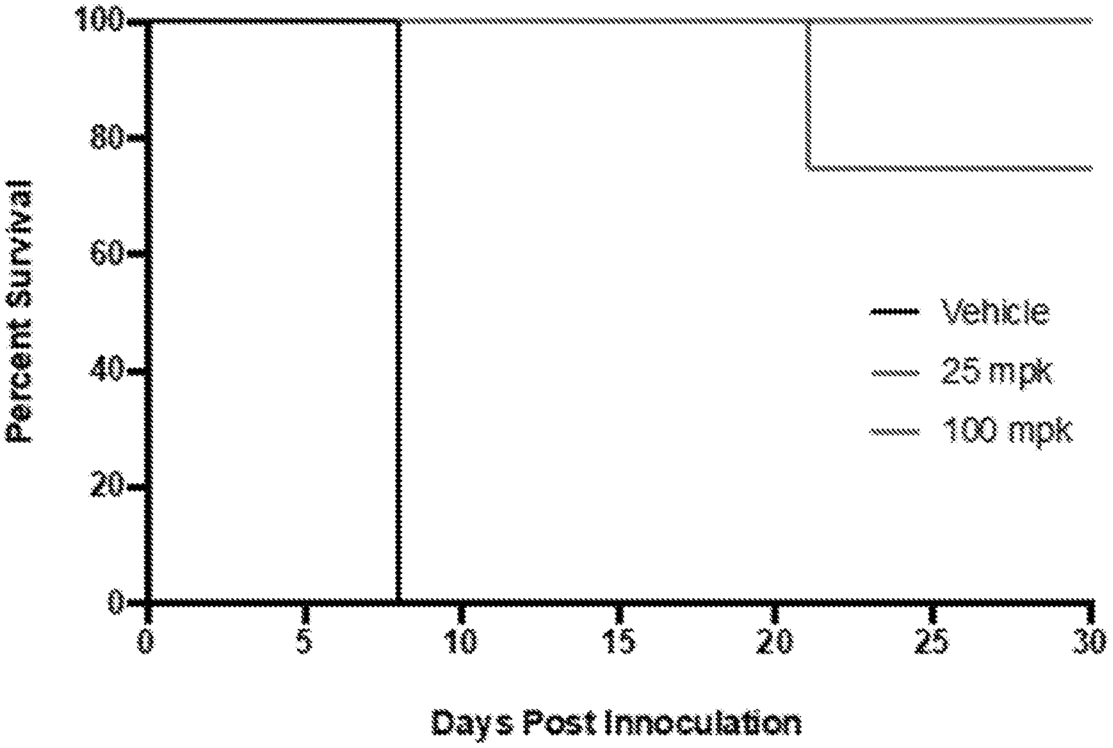
FIG. 7: is an example according to various embodiments illustrating the effect on the survivability of *P. berghei* ANKA infected mice treated with compound 24 s.

In light of in vitro metabolic stability and in vivo efficacy mentioned above, compound 24 s was also administered at 100 and 25 mg/kg to malaria infected mice, and the survival rate was evaluated for 30 days. Phosphate salt of 24 was well tolerated and did not display apparent adverse symptoms such as hunched posture, hypotrichosis and reduced mobility. In addition, administration of salt 24 by these dosing regiments caused no significant weight loss, whereas the body weight of control groups decreased sharply. The mean of survival days in the control group was 8.0 (FIG. 7). FIG. 7 is an example according to various embodiments illustrating the effect on the survivability of *P. berghei* ANKA infected mice treated with compound 24 s. BALB/c females were infected with *P. berghei* ANKA strain expressing luciferase and treated 4 h post-infection with 25 and 100 mg/kg orally once daily for 4 days. The survival curves between compound 24 s at 25 mg/kg and 100 mg/kg were not statistically significantly different using a log-rank (Mantel-Cox) test (p=0.2636). In contrast, administration of salt 24 at the dose of 100 mg/kg prolonged the lives of the mice by 22 days (the end of experiment 30 days) and achieved parasites eradication (data not shown). Importantly, with p.o. administration of 24 s at a lower dose (25 mg/kg), 3 out of 4 mice survived without malaria parasites detected, while all mice succumbed to cerebral malaria in the control group. In comparison, the compound according to Formula 1 cured malaria infection in 4/5 mice when they were exposed to high dose 100 mg/kg twice daily po administration in a previous study, suggesting significant in vivo efficacy improvement for compound 24. This improvement, to some extent, can be explained by the enhanced metabolic stability of 24.

What is claimed is:

1. A compound for the treatment of malaria of the formula:

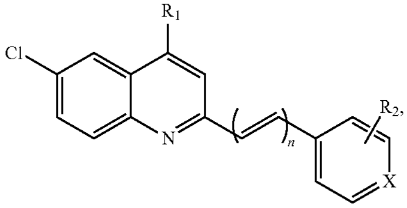

wherein n is 1 or 2;

wherein X is C;

wherein $R_1$ is a moiety comprising a secondary amine and a tertiary amine joined by a $C_2$ to $C_4$ alkyl chain;

wherein $R_2$ is $CF_3$, or a stereoisomer, or pharmaceutically acceptable salt thereof; and wherein the compound exhibits antiplasmodium potency against chloroquine-resistant strains of *P. falciparum.*

2. The compound according to claim 1, wherein $R_1$ is one selected from the group consisting of

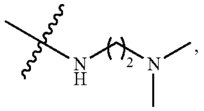
,
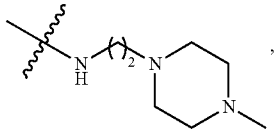
, and
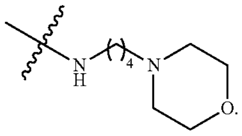

3. The compound according to claim 1, wherein the compound exhibits an $IC_{50}$ against chloroquine-resistant strains of *P. falciparum* of less than or equal to 15 nM.

4. The compound according to claim 1, wherein the compound is

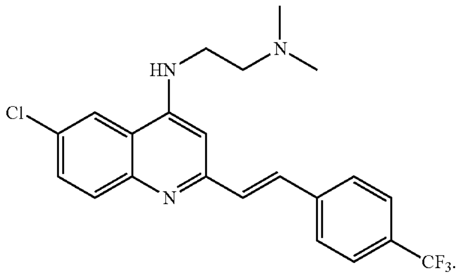 [SMILES: CN(C)CCNc1cc(/C=C/c2ccc(C(F)(F)F)cc2)nc2ccc(Cl)cc12]

5. The compound according to claim 1, wherein the compound is in the form of a phosphate salt.

6. A pharmaceutical composition for the treatment of malaria comprising an effective amount of a compound of the formula:

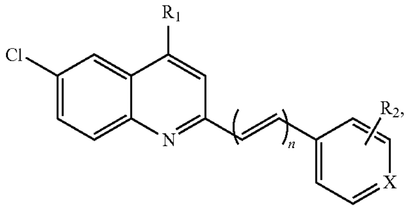

wherein n is 1 or 2;

wherein X is C;

wherein $R_1$ is a moiety comprising a secondary amine and a tertiary amine joined by a $C_2$ to $C_4$ alkyl chain;

wherein $R_2$ is $CF_3$, or a stereoisomer, or pharmaceutically acceptable salt thereof; and wherein the composition exhibits antiplasmodium potency against chloroquine-resistant strains of *P. falciparum.*

7. The pharmaceutical composition according to claim 6, wherein $R_1$ is one selected from the group consisting of

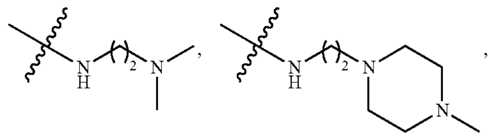

, and

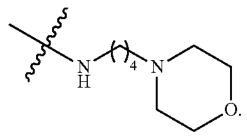

8. The pharmaceutical composition according to claim 6, wherein the composition exhibits an $IC_{50}$ against chloroquine-resistant strains of *P. falciparum* of less than or equal to 15 nM.

9. The pharmaceutical composition according to claim 6, further comprising a pharmaceutically acceptable carrier.

10. The pharmaceutical composition according to claim 6, further comprising a conjunctive anti-malarial agent.

11. The pharmaceutical composition according to claim 6, wherein the compound is

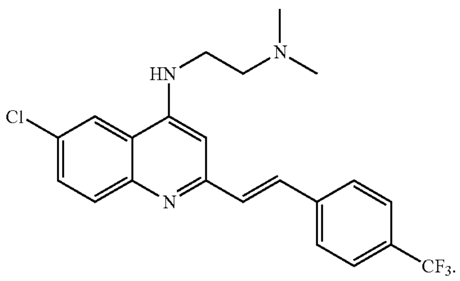

12. The pharmaceutical composition according to claim 6, wherein the compound is in the form of a phosphate salt.

* * * * *